(12) United States Patent
Murillo et al.

(10) Patent No.: US 11,523,818 B2
(45) Date of Patent: Dec. 13, 2022

(54) SUTURE PASSER DEVICES AND METHODS

(71) Applicant: CETERIX ORTHOPAEDICS, INC., Fremont, CA (US)

(72) Inventors: Michael Murillo, Menlo Park, CA (US); Stephen J. Peter, San Francisco, CA (US)

(73) Assignee: CETERIX ORTHOPAEDICS, INC., Fremont, CA (US)

( * ) Notice: Subject to any disclaimer, the term of this patent is extended or adjusted under 35 U.S.C. 154(b) by 670 days.

(21) Appl. No.: 16/392,268

(22) Filed: Apr. 23, 2019

(65) Prior Publication Data

US 2019/0328383 A1 Oct. 31, 2019

Related U.S. Application Data

(60) Provisional application No. 62/663,471, filed on Apr. 27, 2018.

(51) Int. Cl.
*A61B 17/04* (2006.01)
*A61B 17/06* (2006.01)

(52) U.S. Cl.
CPC .... *A61B 17/0483* (2013.01); *A61B 17/06004* (2013.01); *A61B 17/06109* (2013.01); *A61B 17/0469* (2013.01); *A61B 2017/06042* (2013.01)

(58) Field of Classification Search
CPC .......... A61B 17/0483; A61B 17/06004; A61B 17/06109; A61B 2017/06042; A61B 2017/00367; A61B 2017/2925
See application file for complete search history.

(56) References Cited

U.S. PATENT DOCUMENTS

| | | | |
|---|---|---|---|
| 2004/0254605 A1 | 12/2004 | DiFrancesco et al. | |
| 2009/0131956 A1 | 5/2009 | Dewey et al. | |
| 2012/0283753 A1* | 11/2012 | Saliman | A61B 17/0482 606/145 |
| 2017/0020512 A1* | 1/2017 | Murillo | A61B 17/0625 |
| 2017/0027558 A1 | 2/2017 | Murillo et al. | |
| 2017/0333030 A1* | 11/2017 | Bourland, III | A61B 17/062 |

OTHER PUBLICATIONS

IPRP for PCT/US2019/028765 dated Nov. 5, 2020, 13 pages.

\* cited by examiner

*Primary Examiner* — Sarah A Simpson
(74) *Attorney, Agent, or Firm* — Norman F. Hainer, Jr.

(57) ABSTRACT

Suture passer devices and methods of using the devices having one or more protective interlocks preventing or limiting operation of the suture passer when deployment of the needle may damage the apparatus or harm the patient. For example, described herein are suture passer devices that include an interlock preventing deployment of the tissue penetrator (needle) when the jaws are not clamped onto a tissue. Also described herein are interlocks preventing retraction of a jaw axially until the needle is retracted.

15 Claims, 25 Drawing Sheets

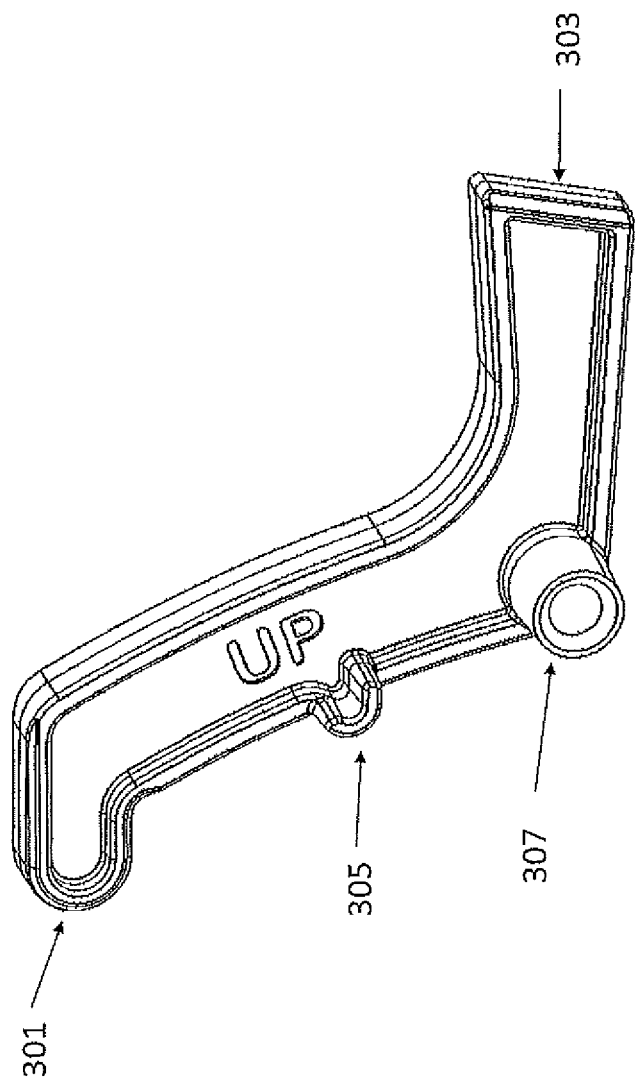

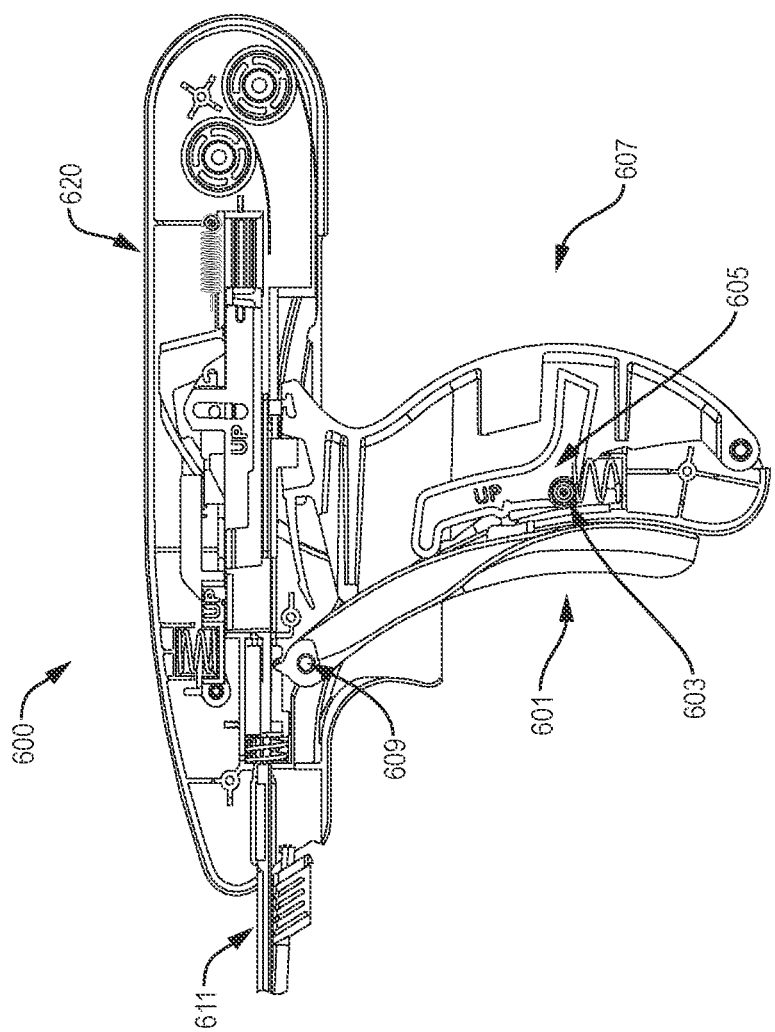

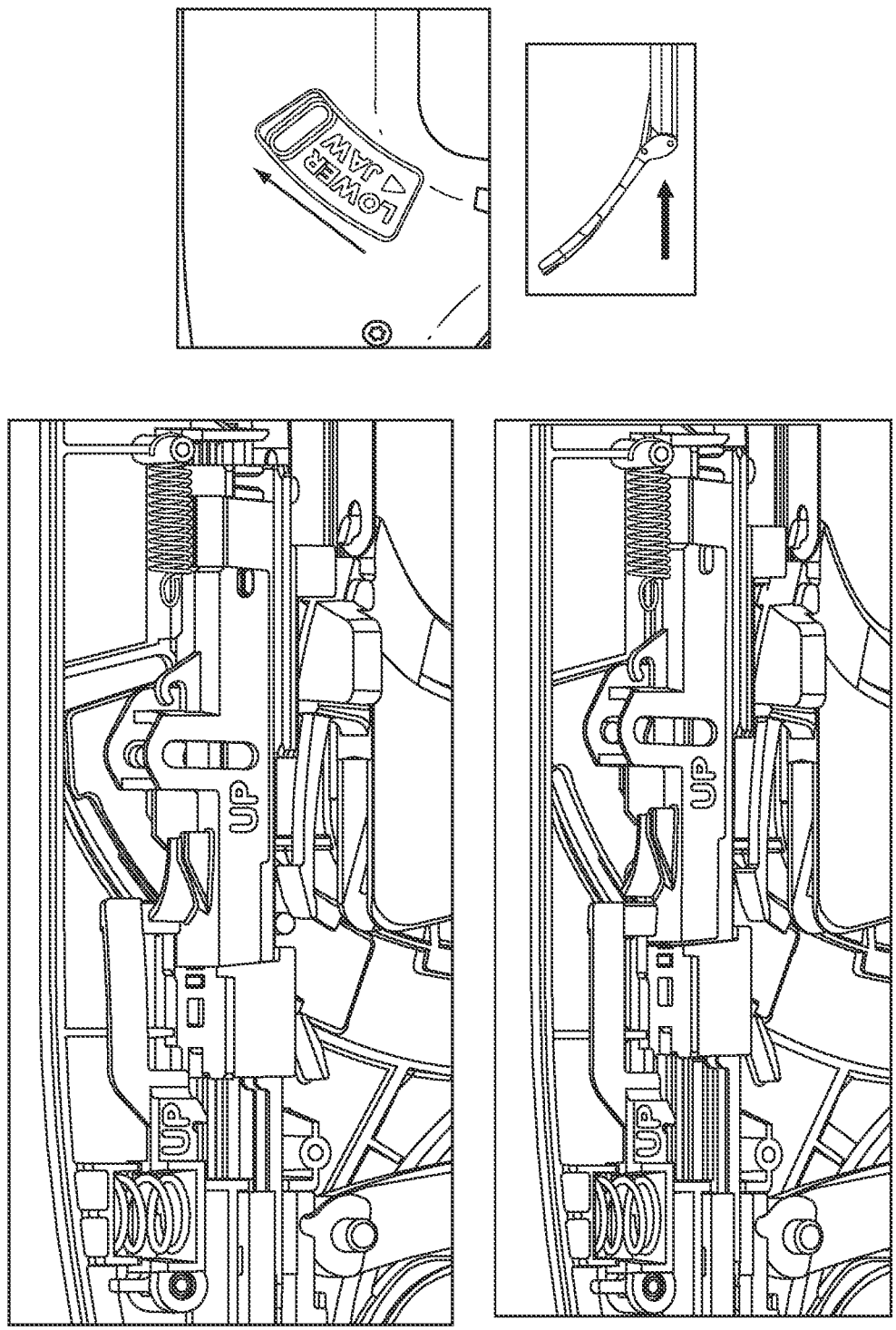

SUTURE PASSER DEVICES AND METHODS

CROSS REFERENCE TO RELATED APPLICATIONS

This application is a non-provisional application which claims priority to U.S. Provisional Application No. 62/663,471 filed Apr. 27, 2018, entitled "Suture Passer Devices and Methods", the full disclosure of which is incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application is related to methods, devices and systems useful for suturing tissue, particularly in difficult to access regions.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

There is a need for new methods and devices for suturing tissue, particularly tissue in difficult to access regions of the body including the joints (shoulder, knee, etc.). The methods and devices described herein address this need.

SUMMARY OF THE DISCLOSURE

The present invention relates to suture passer devices and methods of using the devices.

In one aspect, the present disclosure describes a suture passer device, wherein suture is prevented from being passed without clamping the first and second jaw members. This has the advantage of avoiding a failed stitch due to the suture missing the suture trap. The device includes an elongated body having a proximal end region and a distal end region; a first jaw member extending from the distal end region of the elongated body and configured for angular movement relative to the elongated body; a second jaw member configured to form an opening with the first jaw member when the second jaw member is axially extended; a clamp trigger configured to actuate clamping of the first and second jaw members; a tissue penetrator trigger configured to extend a tissue penetrator between the first and second jaw members when actuated; and a lock between the clamp trigger and the tissue penetrator trigger configured to interact with the clamp trigger and the tissue penetrator trigger to prevent the tissue penetrator from extending until the first jaw member is closed relative to the second jaw member by a predetermined amount.

In another aspect, the present disclosure discloses a method for passing a suture. The method includes at least partially closing a first jaw member of a suture passer, wherein the first jaw member is extended from the distal end region of an elongated body and is configured for angular movement relative to the elongated body; wherein the second jaw is configured to form an opening with the first jaw member; and passing a tissue penetrator between the first and second jaw members when the first jaw member is at least partially clamped with the second jaw member, whereby the tissue penetrator is prevented from being extended without clamping the jaws.

In yet another aspect, the present disclosure includes a suture passer device, wherein the device uses thumb triggers to extend the second jaw member. The device includes an elongated body having a proximal end region and a distal end region; a first jaw member extending from the distal end region of the elongated body and configured for angular movement relative to the elongated body; a second jaw member configured to extend axially relative to the elongated body, wherein the second jaw is configured to form an opening with the first jaw member when the second jaw member is axially extended; a clamp trigger configured to actuate clamping of the first and second jaw members; a tissue penetrator trigger configured to extend a tissue penetrator between the first and second jaw members when actuated; and a thumb trigger configured to extend or retract the second jaw member, wherein the thumb trigger has a first surface and a second surface. The suture passer device also includes a handle, housing a sleeve member, a carriage member and a detent member; and wherein the first surface of the thumb trigger is connected to an outer surface of the sleeve member, wherein an inner surface of the sleeve member is connected with the carriage member and wherein the sleeve member and carriage member both interact with the detent member to maintain a position of an extended second jaw member.

In still another aspect, the present disclosure provides a method for controlling a suture passer having a first jaw member extending from the distal end region of an elongated body and configured for angular movement relative to the elongated body, a second jaw member configured to form an opening with the first jaw member when the second jaw member is axially extended, and a thumb trigger actuated to retract or extend the second jaw member, the method includes: extending the second jaw by pushing the thumb trigger in a first direction; and retracting the second jaw by pushing the thumb trigger in the same direction.

In another aspect, the present disclosure includes a suture passer device, wherein the device is designed to prevent retraction of the second jaw member when the tissue penetrator is extending or extended. The device includes an elongated body having a proximal end region and a distal end region; a first jaw member extending from the distal end region of the elongated body; a second jaw member configured to extend axially relative to the elongated body, wherein the second jaw is configured to form an opening with the first jaw member when the second jaw member is axially extended. The device also includes a tissue penetrator trigger configured to extend a tissue penetrator between the first and second jaw members when actuated; and a thumb trigger configured to retract or extend the second jaw member when actuated, wherein when the tissue penetrator is extended, the second jaw member is blocked from retracting.

In yet another aspect, the present disclosure describes a method for preventing damage to a tissue when using a suture passer device. The suture passer device has a first jaw member extending from the distal end region of an elongated body, a second jaw member configured to extend axially relative to the elongated body, wherein the second jaw is configured to form an opening with the first jaw member when the second jaw member is axially extended. The suture passer device also includes a tissue penetrator trigger configured to extend a tissue penetrator between the first and second jaw members when actuated, and a thumb trigger configured to retract or extend the second jaw member when actuated, the method including: blocking the thumb trigger from actuating to retract the second jaw member when a tissue penetrator is extended.

In yet another aspect, the present disclosure discloses a suture passer device including an elongated body having a proximal end and distal end, the proximal end coupled to a device handle. A first jaw member is coupled to the distal end and may is moved angularly relative to a longitudinal axis of the elongated body. A second jaw member is also coupled to the distal end and may retract in and out of the elongate body and form an opening with the first jaw member. The handle may include a clamp trigger that is operatively coupled to the first jaw member so that actuation of the clamp trigger may move the first jaw member between and open and a clamped configuration relative to the second jaw member. The first and second jaw members are relatively closer to each other in the clamped configuration than the open configuration. The handle may also include a tissue penetrator trigger, operatively coupled to a tissue penetrator disposed at the distal end so as to selectively extend the tissue penetrator between the first and second jaw members. The handle also includes a lock member disposed between the clamp trigger and the tissue penetrator trigger. The lock member may interact with the clamp trigger and the tissue penetrator trigger so as to prevent the tissue penetrator from extending until the first jaw member is in the clamped configuration. The second jaw member may extend and retract axially relative to the elongated body. The lock member may have a first surface configured to interact with the clamp trigger and a second surface configured to interact with the tissue penetrator trigger. The first and second surface may be at opposing ends to each other of the lock member. The lock member may interact with the clamp trigger and tissue penetrator trigger such that when the first jaw member is in the open configuration, the second surface is engaged with the tissue penetrator trigger to block the tissue penetrator from extending. The clamp trigger may include a surface that engages the first surface of the lock while moving the first jaw member towards the clamped configuration, so as to rotate the lock member and disengage the second surface from the tissue penetrator trigger. When in the clamped configuration, the first and second jaw members defines a predetermined opening, which may be an angular opening between 5 degrees and 85 degrees. The first jaw member comprises a tissue penetrator receiving region seen best in FIG. 6A for receiving the tissue penetrator and capturing the suture, and wherein the predetermined opening defines a maximum opening such that the tissue penetrator extends reliably from the second jaw member and through the tissue penetrator receiving region. Should the predetermined opening or angular opening be any wider tissue penetrator may extend away from receiving region and suture transfer from the second jaw member to the first may fail.

In yet another aspect, the present disclosure includes a method for passing a suture, including moving a first jaw member of a suture passer from a first open orientation towards a second jaw member and thereby towards a second clamped orientation, wherein the first and second jaw member extend from a distal end region of an elongate body of a suture passer. A tissue penetrator is then passed between the first and second jaw members when the first jaw member is in the second clamped configuration, whereby the tissue penetrator is prevented from being extended when the first jaw member is in the first open orientation. The step of moving the first jaw member may include actuating a clamp trigger coupled to a proximal end of the elongate body. The step of passing a tissue penetrator may include actuating a tissue penetrator trigger coupled to the proximal end of the elongate body. The suture passer may also include a lock member disposed between the clamp trigger and the tissue penetrator trigger and wherein the lock comprises a lock arm that engages with and thereby inhibits actuation of the tissue penetrator trigger when the first jaw is in the first open orientation. Moving the first jaw to the second clamped configuration may include engaging the clamp trigger with a first portion of the lock member so as to move the lock arm and allow actuation of the tissue penetrator trigger. The lock may be pivotally coupled to the suture passer and the lock arm may extend in a first direction from a center of rotation of the lock member and a second arm may extend in a different direction towards the first portion of the lock, and wherein the lock may rotate to disengage the lock arm from the tissue penetrator trigger. The second jaw may axially extend from within an elongate body of the suture passer before the step of moving the first jaw member.

In yet another aspect, the present disclosure includes a suture passer device with an elongated body having a proximal end region and a distal end region. A first jaw member may be coupled to the distal end region of the elongated body and configured for angular movement relative to the elongated body. A second jaw member may extend axially relative to the elongated body and form an opening with the first jaw member when the second jaw member is axially extended. The suture passer device may also include a thumb trigger that is operatively coupled to the second jaw member so as to extend or retract the second jaw member, wherein the thumb trigger has a first surface and a second surface. The suture passer device may also include a housing with a sleeve member and a carriage member therein. The first surface of the thumb trigger may be communicably coupled to the sleeve member and carriage member, such that activating the thumb trigger axially moves the sleeve member, carriage member and thereby second jaw member. The housing may also include a detent member that engages with an opening of the carriage member to hold the second jaw in an extended configuration. The detent member may be selectively coupled to the carriage member so as to be disengaged from a carriage member opening during retraction of the second jaw member. The detent member may also include proximal tip or end-tip at an end of an arm of the detent member that interacts with a curved rib and ramp disposed on a top surface of the sleeve such that actuation of the thumb trigger to extend the second jaw member slides the sleeve so that the proximal tip moves from a first side of the curved rib and ramp, axially to a second side of the curved rib and ramp and wherein releasing of the thumb trigger to an intermediate position maintains the extended position of the second jaw member with the proximal tip remaining on the second side of the curved rib and ramp.

In yet another aspect, the present disclosure includes a method for controlling a suture passer. Suture passer may have a first jaw member extending from a distal end region of an elongate body, the first jaw may be coupled to the body so as to angularly move relative to the elongated body. A second jaw member may be coupled to the elongate body and may form an opening with the first jaw member when the second jaw member is axially extended. A thumb trigger of the suture passer may be actuated to retract or extend the second jaw member. The method may include extending the second jaw by pushing the thumb trigger in a first direction along an arced path and retracting the second jaw by pushing the thumb trigger in the first direction, followed by releasing the thumb trigger. Extending the second jaw may comprise pushing the thumb trigger to slide a sleeve member and carriage member axially in a distal direction to extend the second jaw member. Retracting may comprise pushing the thumb trigger to slide the sleeve member axially in a distal direction and the step of releasing the thumb trigger may release the sleeve member and carriage member so that they restract in a proximal direction. The sleeve member may be connected to a proximally disposed biasing member configured to draw the sleeve proximally during the step of releasing. The carriage member may be engaged with a detent member when the second jaw member is extended. The carriage member may be disengaged from a detent member during the step of retracting.

In yet another aspect, the present disclosure includes a method for preventing damage to a tissue when using a suture passer device. Suture passer device includes a first jaw member extending from the distal end region of an elongated body, a second jaw member configured to extend axially relative to the elongated body. The second jaw is configured to form an opening with the first jaw member when the second jaw member is axially extended. The suture passer device also includes a tissue penetrator trigger configured to extend a tissue penetrator between the first and second jaw members when actuated, and a thumb trigger configured to retract or extend the second jaw member when actuated. The method may include blocking the thumb trigger from actuating to retract the second jaw member when a tissue penetrator is extended. Blocking may comprise pushing the thumb trigger to extend the second jaw and pressing the tissue penetrator trigger to extend the tissue penetrator, whereby the thumb trigger is blocked from retracting the second jaw member. Blocking may comprise restricting the actuation of the thumb trigger by engaging the tissue penetrator trigger with a protrusion member extended above a first surface of the thumb trigger, whereby the actuation of the thumb trigger to retract a second jaw member is blocked. The tissue penetrator trigger may comprise an outer surface adjacent to the first surface of the thumb trigger, said outer surface interacting with the protrusion member to block the actuation of the thumb trigger to retract a second jaw member.

In yet another aspect, the present disclosure includes a suture passer device with an elongated body having a proximal end region and a distal end region. A first jaw member extends from the distal end region and a second jaw member may extend axially relative to the elongated body. The second jaw is configured to form an opening with the first jaw member when the second jaw member is axially extended. The suture passer device may also include a tissue penetrator trigger configured to extend a tissue penetrator between the first and second jaw members when actuated and a thumb trigger configured to retract or extend the second jaw member when actuated. When the tissue penetrator is extended, the second jaw member is blocked from retracting. The thumb trigger may include a protrusion member extended above a first surface of the thumb trigger and when engaged with the actuated tissue penetrator trigger, the protrusion member may be restricted from movement and thereby actuation of the thumb trigger to retract the second jaw member may be inhibited. The suture passer device may also include a clamp trigger that actuates clamping of the first and second jaw members.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A and 3B illustrate perspective views of a lock of a suture passer.

FIG. 6B is a section view of the suture passer where the first and second jaw members are clamping on a tissue and a suture is passed according to an embodiment of the invention.

FIGS. 15A-15B illustrate how the internal functional components operate to retract a second jaw when a thumb trigger is pushed forward again.

DETAILED DESCRIPTION

Figure 1A:
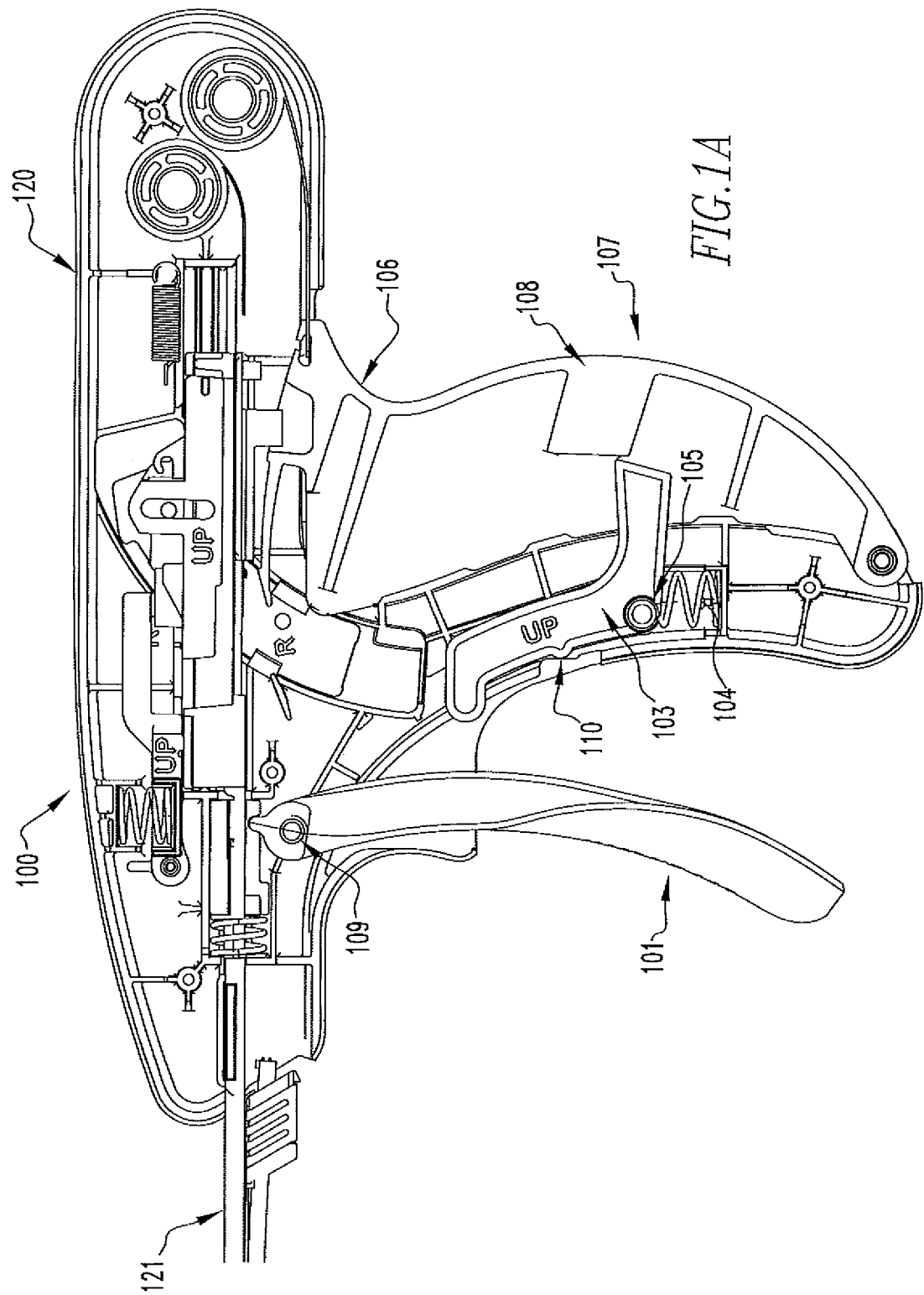
FIG. 1A is a section view of a suture passer, where the first and second jaw members are not clamping on a tissue according to an embodiment of the invention.

Described herein are suture passer devices and methods of using the devices. The devices of the present disclosure have improved reliability, for example, by preventing suture from being passed without clamping the jaw members. The novel design also includes equipping the device with thumb triggers to extend and retract a second jaw member or lower jaw member, which have improved controls of the suture passer. The devices disclosed herein further have the advantages of preventing damage to a tissue by avoiding retraction of the lower jaw or second jaw member when a tissue penetrator is being extended.

In one aspect, the present disclosure includes a suture passer device. The device includes an elongated body having a proximal end region and a distal end region; a first jaw member extending from the distal end region of the elongated body and configured for angular movement relative to the elongated body; a second jaw member configured to form an opening with the first jaw member when the second jaw member is axially extended; a clamp trigger configured to actuate clamping of the first and second jaw members; a tissue penetrator trigger configured to extend a tissue penetrator between the first and second jaw members when actuated; and a lock between the clamp trigger and the tissue penetrator trigger and configured to interact with the clamp trigger and the tissue penetrator trigger to prevent the tissue penetrator from extending until the first jaw member is closed relative to the second jaw member by a predetermined amount.

In some embodiments of the suture devices described herein, the second jaw member of the suture device is configured to extend axially relative to the elongated body.

In some embodiments of the suture devices described herein, the lock of the suture device has a first surface configured to interact with the clamp trigger and a second surface configured to interact with the tissue penetrator trigger.

In some embodiments of the suture devices described herein, when the first and second jaw members are not clamped, the first surface of the lock is disengaged from the clamp trigger and the second surface is engaged with the tissue penetrator trigger to block the tissue penetrator from extending from the second jaw.

In some embodiments of the suture devices described herein, the first surface of the lock is engaged with the clamp trigger while actuating clamping of the first and second jaw members and the second surface of the lock is disengaged from the tissue penetrator trigger allow actuation of the tissue penetrator trigger and to extend a tissue penetrator between the first and second jaw members.

In some embodiments of the suture devices described herein, the engagement of the first surface of the lock with the clamp trigger actuates the rotation of the lock to disengage the second surface of the lock from the tissue penetrator trigger.

In some embodiments of the suture devices described herein, the first jaw member is clamped with the second jaw member to form an opening having a predetermined amount. The predetermined amount is about 5% or more. In certain instances, the predetermined amount is about 5, 10, 15, 20, 25, 30, 35, 40, 45, 50, 55, 60, 65, 70, 75, 80, 85, 90 or 95%. In certain instances, the predetermined amount is defined by the angle formed between the opposing surfaces of both the first jaw member and the second jaw member. The predetermined amount can be 5 degrees or more or between 5 degrees to 85 degrees.

Figure 1B:
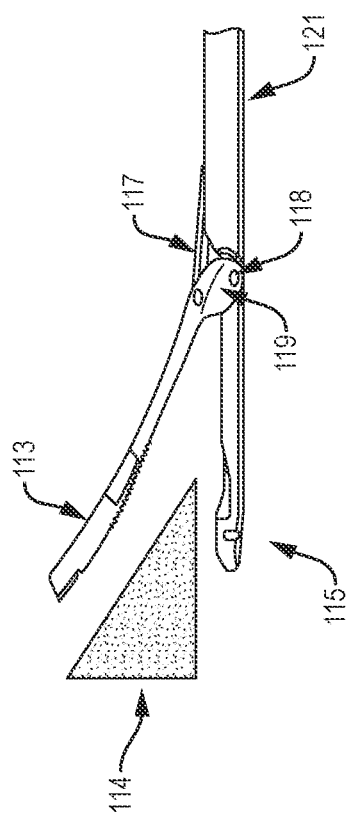
FIG. 1B is a perspective view of a first and second jaw members of a suture passer, where the first and second jaw members are not clamping on a tissue.

FIGS. 1A-1B show portions of a suture passer 100 according to an embodiment of the invention. The suture passer 100 includes a first jaw member 113 and a second jaw member 115 that extend from the distal end of an elongate body region to form a distal-facing mouth into which tissue to be sutured fits. For example, the device has a first (upper) jaw member 113 coupled to and extending distally from the distal end of a more proximal elongate body 121. A second jaw member 115 is shown coupled to the body distal end and extended distally beneath the first jaw member 113.

The first jaw member 113 is held at an angle relative to the long axis of the proximal elongated body. The first jaw member 113 in this example is shown having a hinge region 119 about which the first jaw member 113 may be angled relative to the elongated body 121. In some variations, this hinge region 119 is a pinned hinge; non-pinned (e.g., living hinges) regions may be used. Any appropriate articulating region that allows the first jaw member 113 to move at an angle relative to the proximal portion of the device (e.g., the elongate member) may be used. In some variations this first jaw member 113 is referred to as an upper jaw member, but alternative variations (in which the first jaw member is a lower jaw member) are also possible.

The first jaw member 113 pivots around a hinge point 118, and is controlled by a pulling member 117 that pushes and/or pulls proximally and/or distally to control the angle of the first jaw member 113 relative to the second jaw member 115. The pulling member 117 may include a shaft, wire, tendon, tube, cannula, or the like, and may extend to the proximal end of the device where it can be controlled.

The second jaw member 115 is configured to slide proximally towards and into the proximal elongated body 121 of the device. The second jaw member 115 typically moves axially, in the direction of the proximal-distal axis of the suture passer 100. Stated otherwise, the second jaw member 115 moves axially towards and away from the handle housing 120. The second jaw member 115 shown in FIG. 1B as well as FIG. 8A can retract completely into, and extend out of, the elongated body 121.

FIG. 1A illustrates an embodiment of a handle for deployment of suture passer. The clamp trigger 101 is a squeeze handle that controls the angle of the first jaw member 113 relative to the elongated body 121. The clamp trigger 101 can move around the pivotal point 109 when pulled or released. A tissue penetrator trigger 107 controls the extension of the tissue penetrator (shown in FIG. 6A). In this embodiment, a lock 103 is located between the clamp trigger 101 and the tissue penetrator trigger 107. In FIG. 1A, the lock control 103 is connected to a spring 104 and can be rotated around pivotal point 105 by the clamp trigger 101. Spring 104 may always be in a compressed state, configured to bias the lock 103 in the orientation as shown in FIG. 1A and inhibit actuation of the trigger 107. The lock control 103 is arranged to either allow or block the actuation of the tissue penetrator trigger 107. FIG. 1A and FIG. 1B illustrates a first configuration of the device, where the clamp trigger 101 is not engaged and the first jaw and second jaw members are not clamped to tissue 114 as shown in FIG. 1B. This first configuration wherein the jaws are not clamped or are in an open configuration is defined as a distance or angular orientation/separation between the first and second jaws such that a tissue penetrator extending from the second jaw 115 towards the first jaw 113 may not be reliably be captured by the first jaw 113. This may include not being adequately captured by the first jaw 113 or may miss a capture location/region associated with the first jaw 113. Hence tissue penetrator activation is inhibited until the first jaw is positioned close enough to the second jaw such that the first jaw's suture and tissue penetrator capture location may reliably be targeted as the tissue penetrator extends from the second jaw 115. In this embodiment, the lock 103 blocks or abuts a portion of the tissue penetrator trigger 107, thus preventing a tissue penetrator being extended and a suture being passed. In an alternative embodiment, the lock 103 can be in electronic communication with the clamp trigger and tissue penetrator trigger to either allow or block the actuation of the tissue penetrator trigger.

Figure 2:
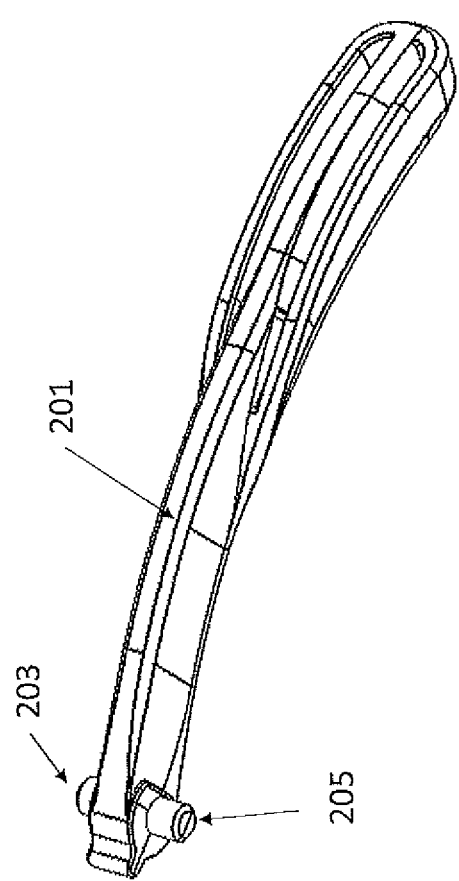
FIG. 2 is a perspective view of a clamp trigger of a suture passer according to an embodiment of the invention.

FIG. 2 illustrates a perspective view of a clamp trigger 101. The clamp trigger 101 has a surface 201, which may interact with the lock 103. The pivotal joints 203 and 205 are connected to the housing 120, and more specifically are configured to rotatingly couple to pivot 109 as shown in FIG. 1A, to allow the clamp trigger 101 to pivot when squeezed or pulled. Surface 201 defines a smooth elongate surface such that while clamp trigger 101 is pivoting surface 201 may engage and slide along a lock surface while simultaneously begin to move or rotate lock 103 around pivot 105. Rotation of lock 103 may also further compress spring 104 and begin to release trigger 107.

Figure 3B:
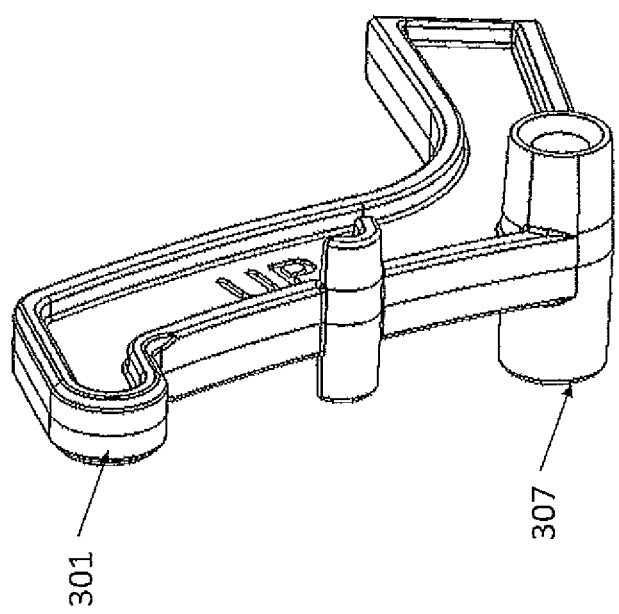

FIGS. 3A-3B illustrate perspective views of a lock 103. The lock 103 has a first surface or a first end region 301, which may interact with the clamp trigger 101 and more specifically with the surface 201. First end region 301 defines a curve surface configured to abut surface 201 and aid continuous contact between the two surfaces (201 and 301) as they slide and rotate relative to each other as the clamp trigger 101 pivots around pivot 109 and as the lock 103 rotates. The second surface or the second end region 303 is configured to interact with the tissue penetrator trigger 107 and defines a substantially flat surface for selective engagement with rib 108. The pivotal member 307 allows the lock 103 to rotate when the first end region 301 is engaged with the clamp trigger 101. The protrusion member 305 may serve to prevent the pivotal movement of the lock 103 when the surface or end 301 does not interact with the clamp trigger. Protrusion member 305 may rest on reference surface 110 serving as a reference marker to ensure lock 103 is assembled correctly within the housing 120 and position of lock 103 is controlled within the handle. Having a method to control this dimension allows the ability to determine a specific angle (or position) for trigger 101 at which the movement restriction on trigger 107 is released. Stated otherwise, a measureable of controllable offset distance between a distal-most surface of member 305 and distal-most surface of the first end region 301 after housing 120 assembly and closure will ensure that lock 103 is correctly installed within housing 120.

FIG. 3B shows another perspective view of the lock 103. Lock 103 may be generally L shaped, with a first arm terminating in first end region 301 and a second arm terminating in second end region 303.

Figure 4:
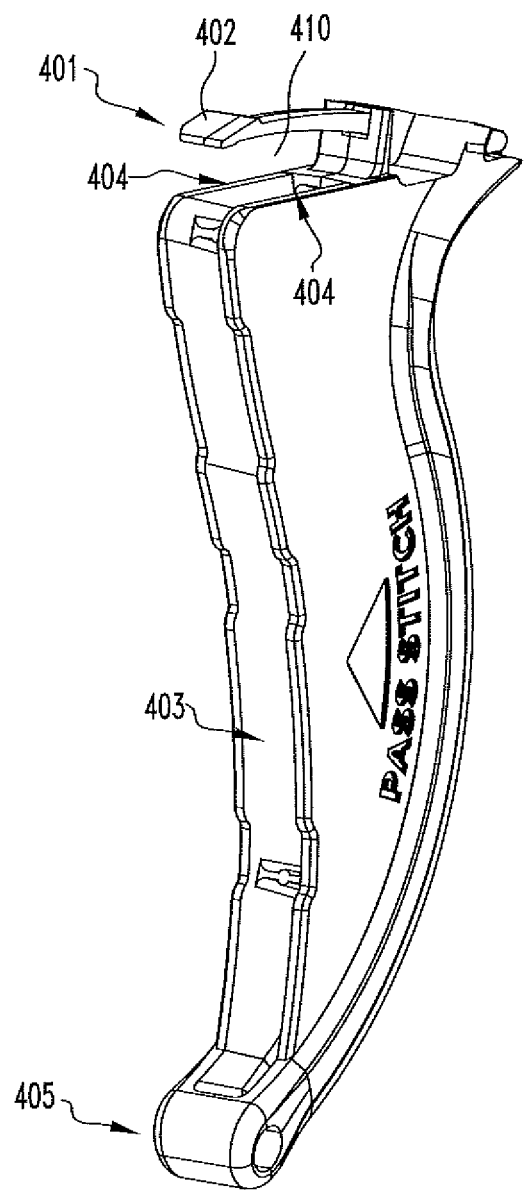
FIG. 4 is a perspective view of a tissue penetrator trigger of a suture passer.

FIG. 4 illustrates a perspective view of a tissue penetrator trigger 107. The tissue penetrator trigger 107 has an elongate arm 401, which may include a distal snap 402 for selectively engaging a portion of housing 120. Elongate arm 401 extends substantially parallel to top surface 404 so as to define an opening 410. Elongate arm 401 terminates with a snap feature that interacts with a rib or surface on the handle to provide tactile feedback to the user that the penetrator trigger 107 has reached the end of travel. Top surface(s) 404 are configured to interact with thumb trigger, discussed in later figures. Tissue penetrator trigger 107 includes a hollow space 403 which allows passage of the lock second region 303 therein, and thereby allows the interaction of the tissue penetrator trigger 107 with the lock 103. The pivotal point 405 allows the tissue penetrator trigger 107 to rotate when squeezed. Hollow space 403 comprises at least one rib or protrusion 108 configured to abut lock second surface 303 when the jaws (113 and 115) are in a first unclamped configuration. Activation or movement of tissue penetrator trigger 107 is thereby inhibited. Best seen in FIG. 1A, the at least one rib or protrusion 108 is positioned such that movement of the clamp trigger 101 to a second (squeezed) position moves the lock surface 303 away from the at least one rib 108 such that the tissue penetrator trigger 107 may move; the second position being defined such that the jaws (113, 115) are in a second or clamped configuration, sufficient for suture capture.

Figure 5A:
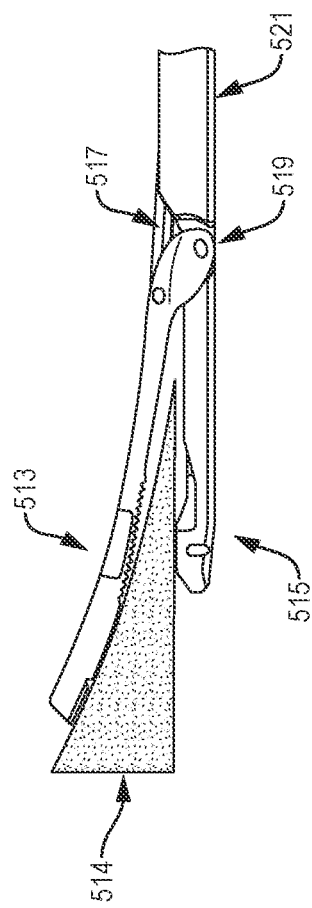
FIG. 5A is perspective view of a first and second jaw members of a suture passer, where the first and second jaw members are clamping on a tissue
Figure 5B:
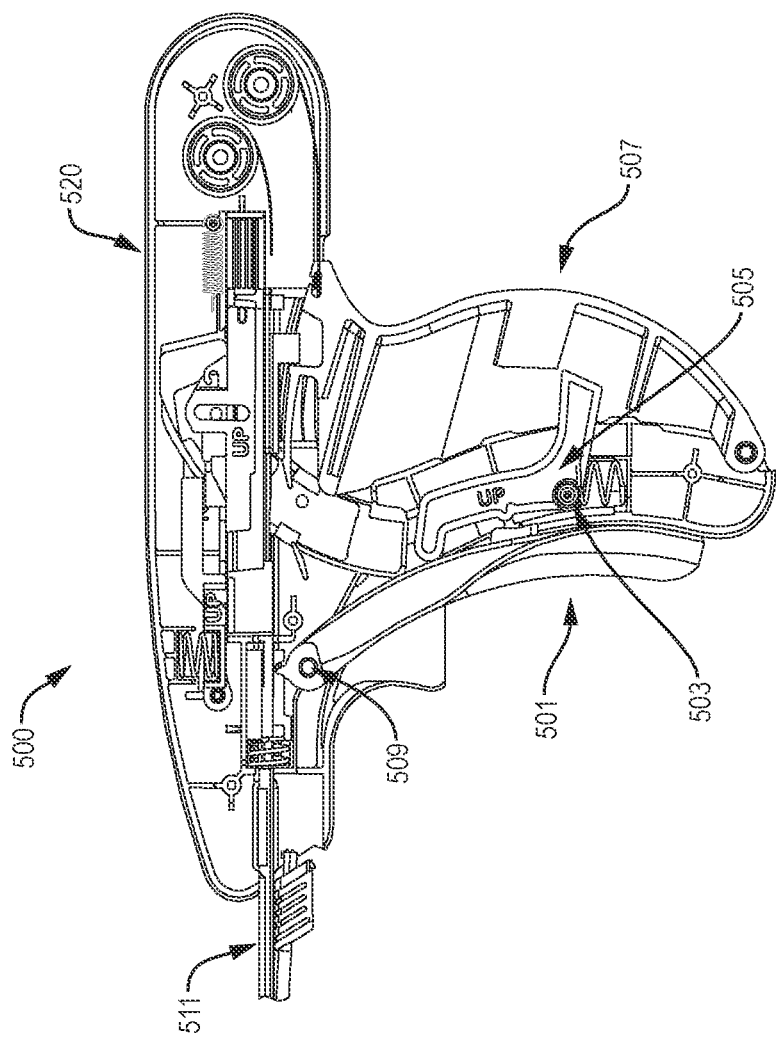
FIG. 5B is a section view of a suture passer handle, where the first and second jaw members are clamping on a tissue according to an embodiment of the invention.

FIGS. 5A-5B illustrate a perspective view of partially closed first and second jaw members disposed on a body distal end 521 on a tissue 514 and the corresponding operation of the suture passer 500 when the first and second jaw members are sufficiently clamped on a tissue according to an embodiment of the invention. This may be defined as the second or clamped configuration. The first jaw member 513 pivots around a hinge point 519, and is controlled by a pulling member 517 that pushes and/or pulls proximally and/or distally to control the angle of the first jaw member 513 relative to the second jaw member 515.

FIG. 5B shows housing 520 coupled to a proximal end of elongate body 511 when the first and second jaw members are partially closed on a tissue by pulling the clamp trigger 501, the clamp trigger 501 is shown pivoted around pivot 509 and engaged with the first surface or first end region of the lock (such as 301 best seen in FIG. 3A). As shown, clamp trigger 501 has further overcome spring bias from spring 104 and moved the lock 505 so to disengage the second region 305 from the tissue penetrator trigger 507 by rotating the lock about pivot 503 and away from the path of the tissue penetrator trigger 507. For example, the second surface or end of the lock is rotating away such that the tissue penetrator trigger 507 when squeezed, is no longer inhibited by the lock. Second surface is moved to a position that no longer interferes with internal features of the trigger 507 and thereby no longer inhibits activation of trigger 507.

Figure 6A:
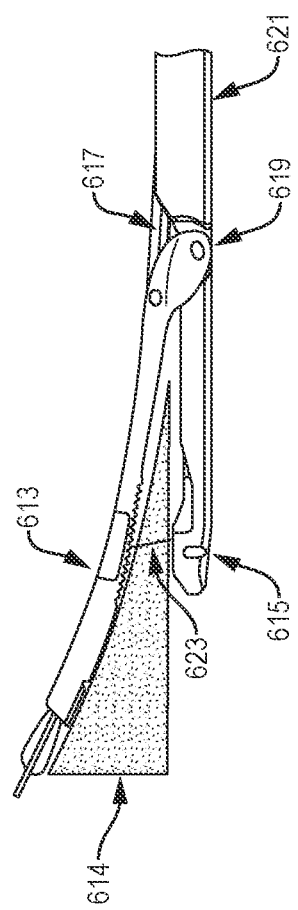
FIG. 6A is a perspective view of partially closed first and second jaw members of a suture passer, where the first and second jaw members are clamping on a tissue and a suture is passed.

FIGS. 6A-6B further illustrate the operation of the suture passer 600 according to an embodiment of the invention. In this perspective view of the device, the first and second jaw members are disposed on a body distal end 621 and are clamped on a tissue 614. The first jaw member 613 pivots around a hinge point 619, and is controlled by a pulling member 617 that pushes and/or pulls proximally and/or distally to control the angle of the first jaw member 613 relative to the second jaw member 615. More specifically first and second jaw members are disposed such that spacing between them is limited to a maximum predetermined distance such that successful transfer of suture from the second jaw member to the first jaw member is achieved. First jaw member 613 may include a suture capture region for receiving the tissue penetrator 623. Should opening be more than the maximum predetermined amount, tissue penetrator 623 may fail to interact with the first jaw member or may interact with a region of the first jaw member outside of the suture capture region and therefore fail to capture the suture. An example suture capture region may be seen on FIG. 6A as boundary lines on first jaw member 613 directly adjacent where tissue penetrator 623 intersects with first jaw member 613. Housing 620 is coupled to body proximal end 611. The clamp trigger 601 is engaged with the first surface or first end of the lock 605, so that the lock 605 has moved or rotated to second location and disengaged from an internal feature such as rib 108 associated with the tissue penetrator trigger 607. Lock 605 pivots around point 603 and clamp trigger 601 pivots around pivot 609. The tissue penetrator trigger 607 is shown actuated, so that a tissue penetrator 623 may extend from the first jaw 613 to the second jaw 615, and suture is passed. Lock second region 303 is shaped so as to easily pass through hollow space 403 and below rib 108 as trigger 607 is activated.

In another aspect, the present disclosure provides a method for passing a suture. The method includes at least partially closing a first jaw member of a suture passer, wherein the first jaw member is extended from the distal end region of an elongated body and is configured for angular movement relative to the elongated body; and a second jaw member, wherein the second jaw is configured to form an opening with the first jaw member; and passing a tissue penetrator between the first and second jaw members when the first jaw member is at least partially clamped with the second jaw member, whereby the tissue penetrator is prevented from being extended without clamping the jaws.

In some embodiments of the method provide herein, the suture passer, which includes a clamp trigger configured to move the first jaw member in angular movement relative to the elongated body; a tissue penetrator trigger configured to extend a tissue penetrator between the first and second jaw members when actuated; and a lock between the clamp trigger and the tissue penetrator trigger and configured to interact with the clamp trigger and the tissue penetrator trigger to prevent the tissue penetrator from extending until the first jaw member is closed relative to the second jaw member by a predetermined amount. The predetermined amount can be at least about 5% or more. In certain instances, the predetermined amount is about 5, 10, 15, 20, 25, 30, 35, 40, 45, 50, 55, 60, 65, 70, 75, 80, 85, 90 or 95%.

In some embodiments of the method provide herein, the clamp trigger is configured to actuate clamping of the first and second jaw members.

In some embodiments of the method provide herein, the lock has a first surface configured to interact with the clamp trigger and a second surface configured to interact with the tissue penetrator trigger.

In some embodiments of the method provide herein, when the first and second jaw members are not clamped, the first surface of the lock is disengaged from the clamp trigger and the second surface is engaged with the tissue penetrator trigger to block the tissue penetrator from extending from the second jaw.

In some embodiments of the method provide herein, wherein the first surface of the lock is engaged with the clamp trigger to actuate clamping of the first and second jaw members and the second surface of the lock is disengaged from the tissue penetrator trigger to actuate the tissue penetrator trigger and to extend a tissue penetrator between the first and second jaw members.

In some embodiments of the method provide herein, the engagement or interaction of the first surface of the lock with the clamp trigger actuates the rotation of the lock to disengage the second surface of the lock from the tissue penetrator trigger. In this embodiment, the lock is no longer in the path the tissue penetrator trigger to block the actuation of the tissue penetrator trigger.

In some embodiments of the method provide herein, the second jaw member is configured to extend axially relative to the elongated body.

In some embodiments of the method provide herein, a suture is passed by the tissue penetrator deployable held with a distal tip retracted entirely within either the first or the second jaw member.

In some embodiments of the method provide herein, wherein the tissue penetrator is deflected as it extends from within either the first or second jaw member to extend between the first and second jaw member.

In another aspect, the disclosure provides a suture passer device. The device includes an elongated body having a proximal end region and a distal end region; a first jaw member extending from the distal end region of the elongated body and configured for angular movement relative to the elongated body; a second jaw member configured to extend axially relative to the elongated body, wherein the second jaw is configured to form an opening with the first jaw member when the second jaw member is axially extended; a clamp trigger configured to actuate clamping of the first and second jaw members; a tissue penetrator trigger configured to extend a tissue penetrator between the first and second jaw members when actuated; and a thumb trigger configured to extend or retract the second jaw member, wherein the thumb trigger has a first surface and a second surface; a housing comprising a sleeve member, a carriage member and a detent member; and wherein the first surface of the thumb trigger is engaged with the sleeve member, wherein the inner surface of the sleeve member is connected with a carriage member, wherein the carriage member is engaged with the detent member to actuate the second jaw member to extend or retract.

In some embodiments of the device provided herein, the thumb trigger when pushed moves the sleeve member, which moves the carriage member to actuate the second jaw member to extend or retract.

In some embodiments of the device provided herein, the carriage member is engaged with a detent member to extend a second jaw member.

In some embodiments of the device provided herein, the carriage member is disengaged from a detent member to retract a second jaw member.

In some embodiments, the device provided herein further includes a lock configured to interact with the clamp trigger and the tissue penetrator trigger to prevent the tissue penetrator from extending until the first jaw member is closed relative to the second jaw member by a predetermined amount.

Figure 7:
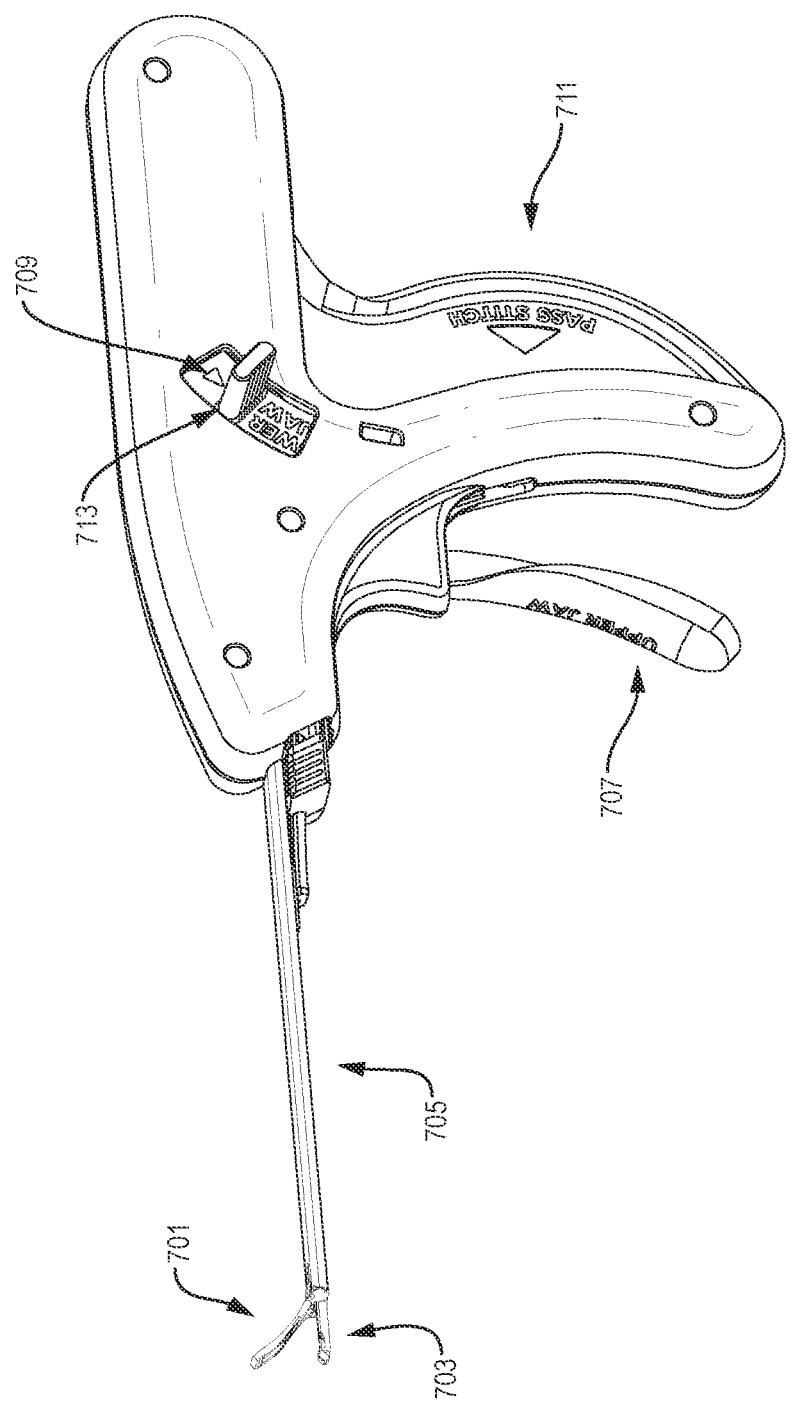
FIG. 7 is a perspective view of a suture passer with a thumb trigger according to an embodiment of the invention.

FIG. 7 illustrates a perspective view of an embodiment of a suture passer equipped with thumb triggers 709 The thumb triggers 709 each have a pushing button 713. The thumb triggers 709 when pushed can extend or retract the second jaw member 703. Not seen from this angle, a second thumb trigger 709 may be disposed on the back side of suture passer. Suture passer includes clamp trigger 707, tissue penetrator trigger 711, elongate body 705 coupled to a distal end of handle housing and a first and second jaw (701 and 703 respectively) coupled to distal end of elongate body 705.

Figure 8A:
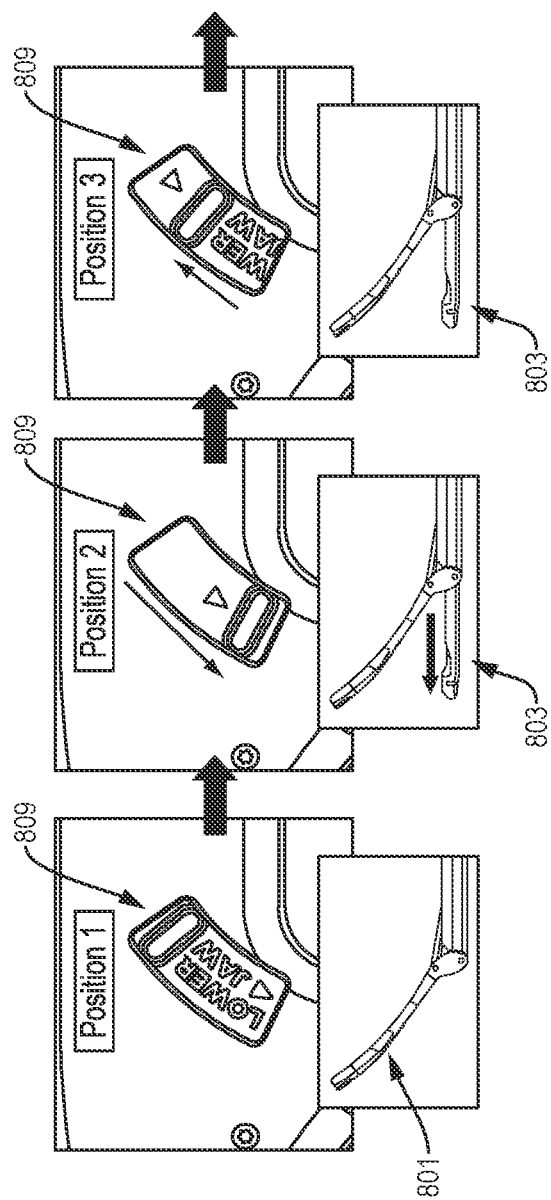
FIGS. 8A-8B illustrate the operation of a thumb trigger.
Figure 8B:
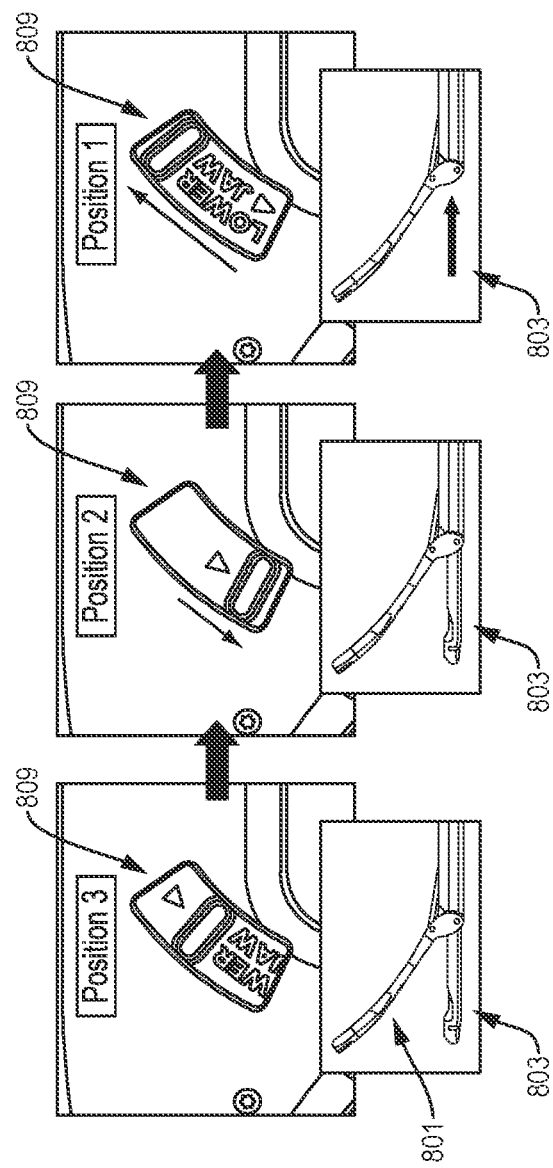

FIGS. 8A-8B illustrate the operation of the thumb trigger 809 to extend or retract the second jaw member 803. First jaw member 801 is also shown. In FIG. 8A, with the second jaw (lower jaw) member retracted, the thumb trigger 809 begins in its fully-back position (position 1). A thumb trigger 809 is advanced or pressed forward and along the curved path to extend the second jaw member 803 (position 2). When released, the thumb trigger 809 returns to an intermediate position (position 3) and the second jaw 803 remains extended. In FIG. 8B, to retract the second jaw 803, thumb trigger 809 is advanced again (position 2) and released to retract the second jaw member 803, returning the thumb trigger 809 to position 1. In other embodiments, the thumb trigger(s) 809 may remain at the forward position (position 2) after extending the second jaw member 803, or they may fully return (position 1) after extending the second jaw member. Orientation and pathway of the thumb trigger button(s) 713 as the button is advanced and retracted may be at a non-zero angle relative to the body long axis and may travel along a curved pathway, configured so that a person's thumb may easily reach said button(s) 713 with the same hand that grasps the tissue penetrator trigger 707. Hence the pathway orientation and curve is such that there is a consideration of a distance range between trigger curved surface portion 106 and pathway orientation so as to keep it within a range of one to two inches.

Figure 9:
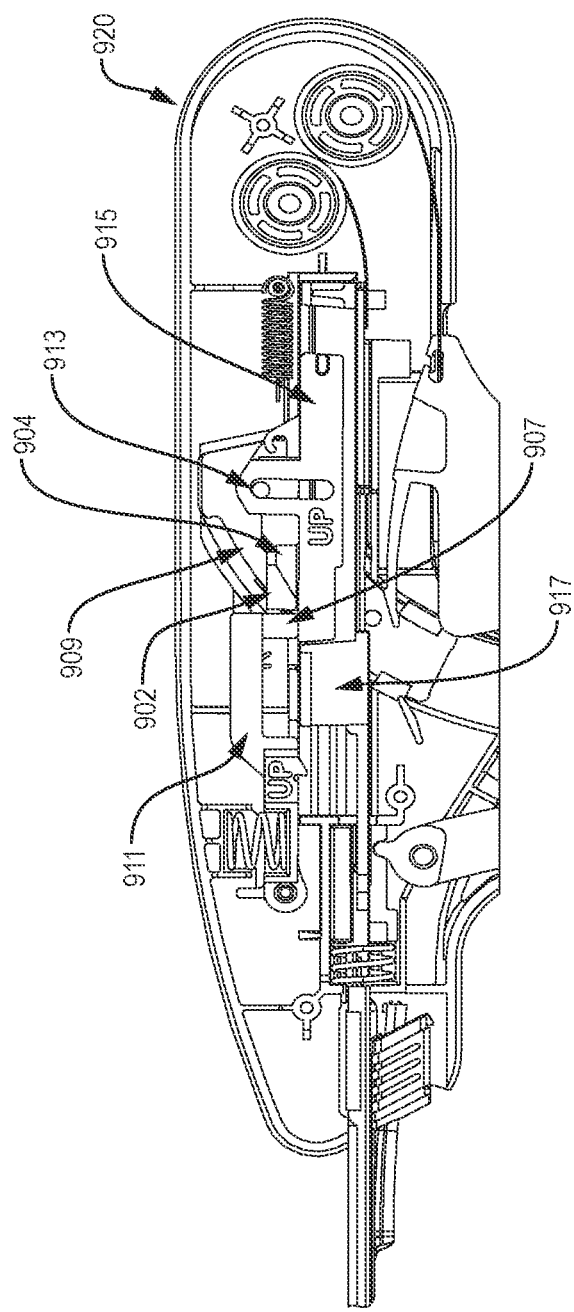
FIG. 9 is a section view of the internal functional components when thumb triggers are used, in accordance with at least some embodiments.

FIG. 9 illustrates a section view of functional internal components when thumb triggers are used. The housing 920 may contains two thumb triggers 909 (only one is shown), one on each lateral side of housing 920. Generally advancing the thumb trigger 909 along the defined pathway, axially moves a sleeve member 915 disposed within the housing 920, the sleeve member 915 coupled to a carriage 917, the carriage 917 coupled to the second jaw member. Axial motion of the carriage 917 axially slides the second jaw to as to advance and retract second jaw into and out of elongate body. A flexible arm associated with the detent member 911 flexes around a series of channels and protrusions on the sleeve member 915 so as to selectively advance and retract the second jaw member as described in FIGS. 8A and 8B. Shown in FIG. 9 thumb triggers 909 are connected by protrusion members 913 to slots on sleeve member 915. Protrusion member 913 and slots are configured such that advancing thumb trigger(s) 909 axially slides sleeve member which thereby axially slides carriage 917 to actuate the jaw member. The position of the carriage 917 controls whether the second jaw member is extended or retracted. The detent member 911, including proximal tip or tooth 907 interacts with the ribs 902 and ramps 904 on the sleeve member 915 to control the position of the carriage 917 and thereby the axial position of the second jaw.

Figure 10:
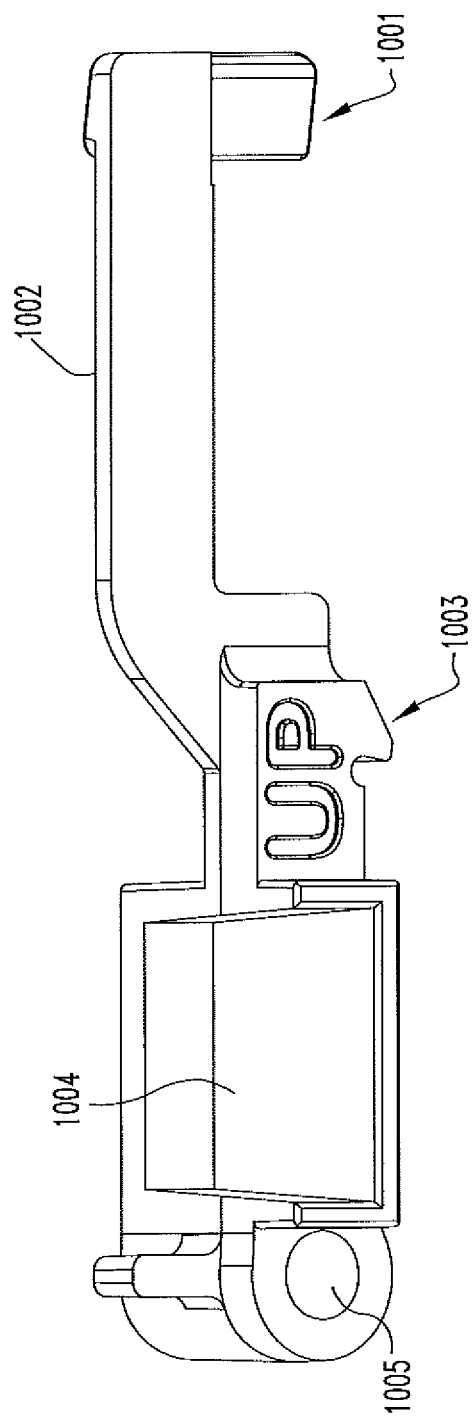
FIG. 10 is a perspective view of a detent member.

FIG. 10 is a perspective view of detent member 911. A first detent tip or tooth 1001 is disposed at an end of arm 1002, the first tooth 1001 designed to interact with the sleeve member 915 so as to selectively retain an axial position of the carriage 917 and thereby a position of the second jaw 115 upon releasing engagement with the thumb trigger, per FIG. 8A, position 3. First detent tooth 1001 may extend substantially orthogonally to the arm 1002, so as to extend towards a top surface of sleeve member 915 and more specifically towards ribs 902 and ramps 904. Detent member 911 also includes a second detent tooth or tip 1003 configured to engage with the carriage member 917 to control the movement of the second jaw member (More detail thereof in later figures). Second tooth 1003 may have a leading sloped surface and a trailing orthogonal surface relative to a top surface of the carriage 917. Detent member 911 also includes a nest 1004 for housing a portion of a biasing member and tubular opening 1005 for rotatingly coupling detent member 911 to housing 920 via pin or protrusion (not shown). In operation detent member 911 may have some limited rotation so as to compress biasing member, biasing member (best seen in FIG. 9) configured to maintain engagement of first and second detent teeth 1001 and 1003 with a feature of the sleeve member 915 and carriage 917 respectively.

Figure 11A:
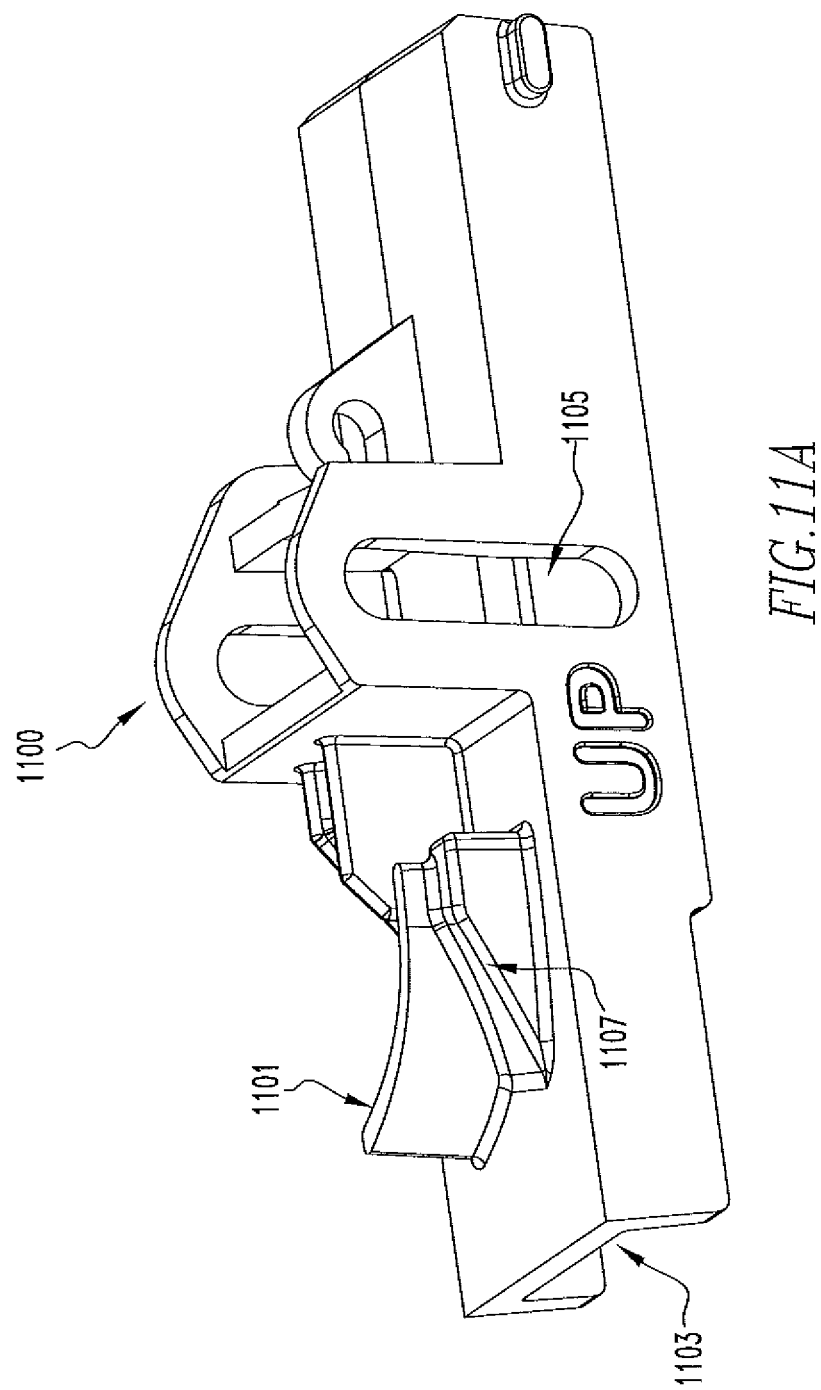
FIGS. 11A and 11B are perspective views of a sleeve member.
Figure 11B:
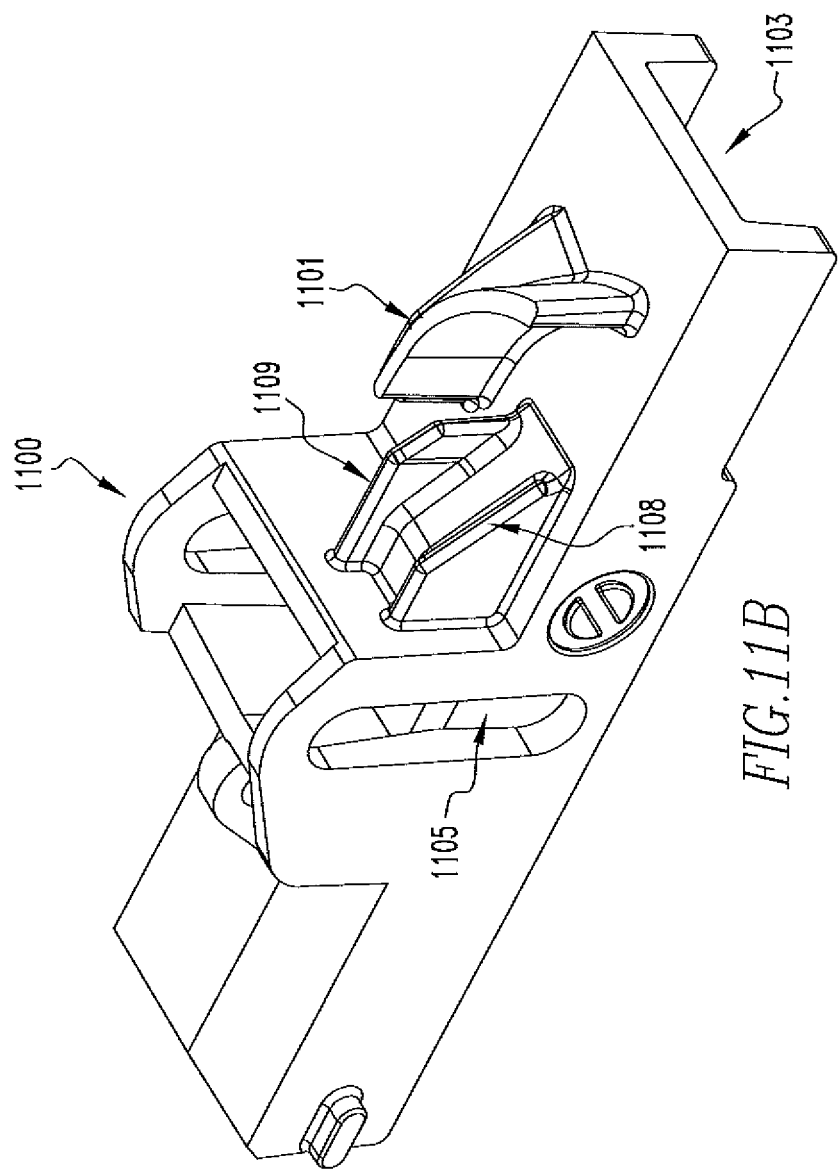

FIGS. 11A and 11B are perspective views of a sleeve member 1100. Curved rib 1101 and ramp 1107 are formed so as to be one continuous protrusion, which selectively interacts with the detent member 911 while advancing the second jaw member. More specifically curved rib 1101 and ramp 1107 selectively interact with first detent tooth 1001. The slot 1105 is configured to engage with the thumb trigger to allow the thumb trigger to control the movement of the sleeve and carriage member. The under surface 1103 may be in contact or connected with a carriage member 917. FIG. 11B illustrates a second ramp 1108 and second rib 1109 configured to interact with the first detent tooth 1001 while the second jaw member is being retracted, as will be described in later figures in more detail. Curved rib 1101 and second rib 1109 are laterally spaced so as to allow first detent tooth 1001 to pass therebetween.

Figure 12:
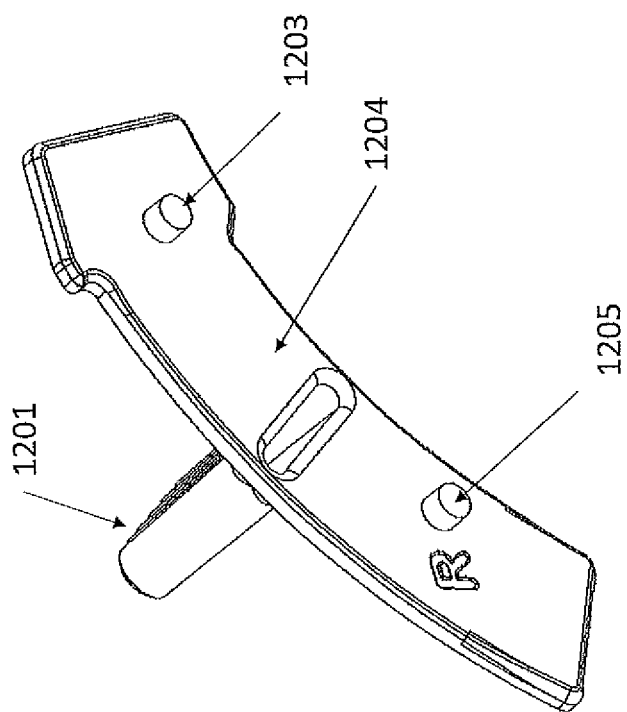
FIG. 12 is a perspective view of a thumb trigger.

FIG. 12 is a perspective view of a thumb trigger 1201. The thumb trigger 1209 has a push button, protrusion member 1203 and 1205 and a first surface 1204. The protrusion member 1205 is configured to interact or selectively engage with a tissue penetrator trigger to prevent the retraction of the second jaw member when a tissue penetrator is extended (disclosed in later figures). Protrusion member 1203 is configured to interact with a slot in sleeve member to drive axial advancement and retraction of second jaw.

Figure 13:
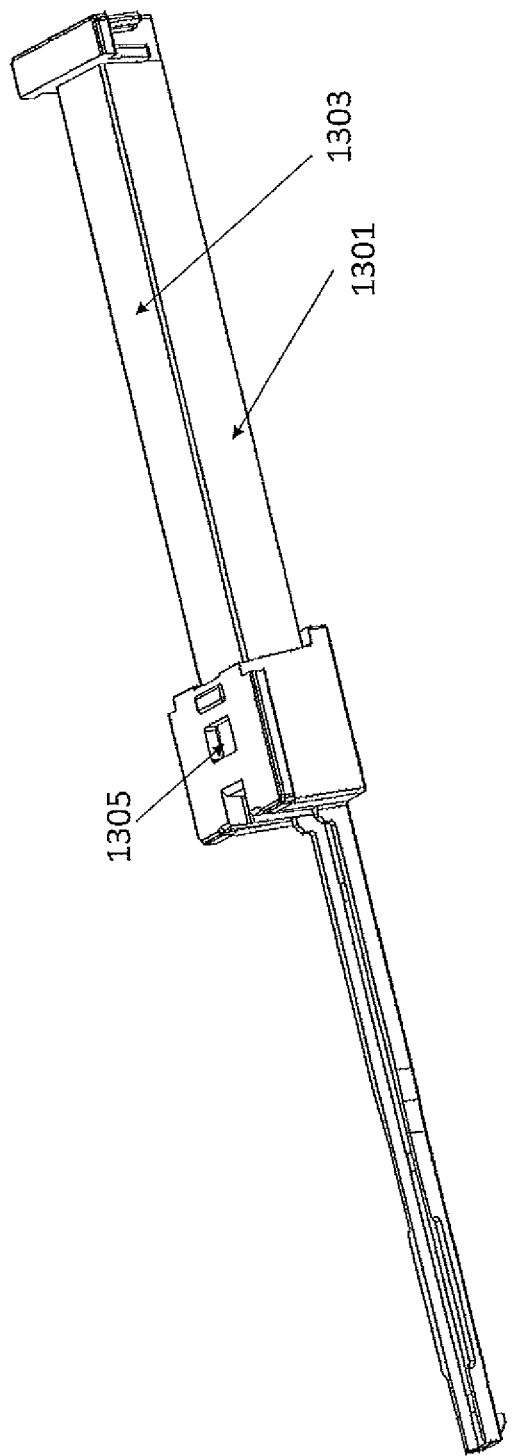
FIG. 13 is a perspective view of a carriage member.

FIG. 13 is a perspective view of carriage member having surface 1301 and 1303 for slidingly engaging with the sleeve member. More specifically surfaces 1301 and 1303 slidingly fit within mating feature associated with surface 1103. Opening 1305 on the carriage member is sized to engage with the second detent tip 1003 of the detent member 911 while second jaw member in extended position.

Figure 14A:
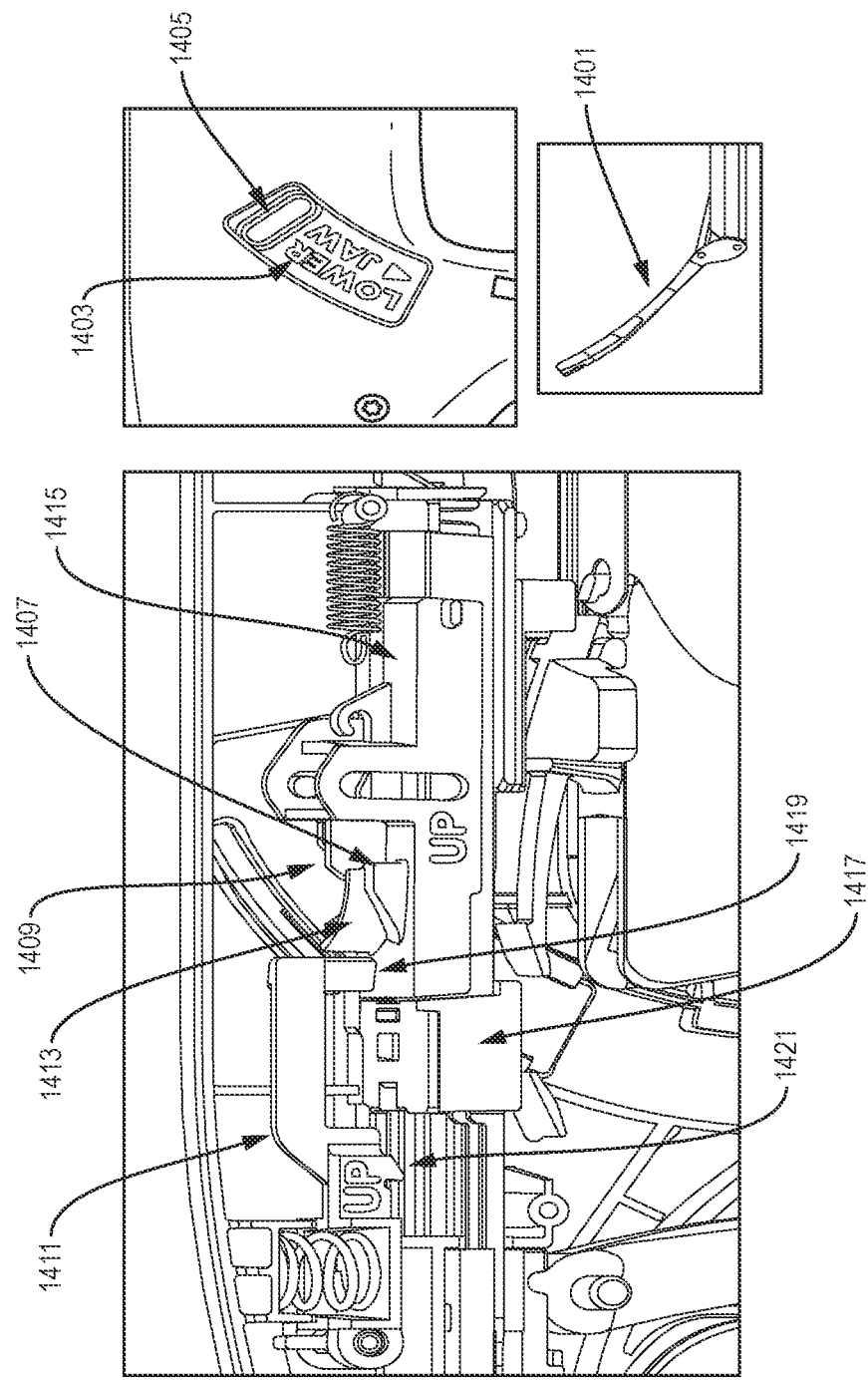
FIGS. 14A-14C illustrate how the internal functional components operate to extend a second jaw when a thumb trigger is pushed forward.
Figure 14B:
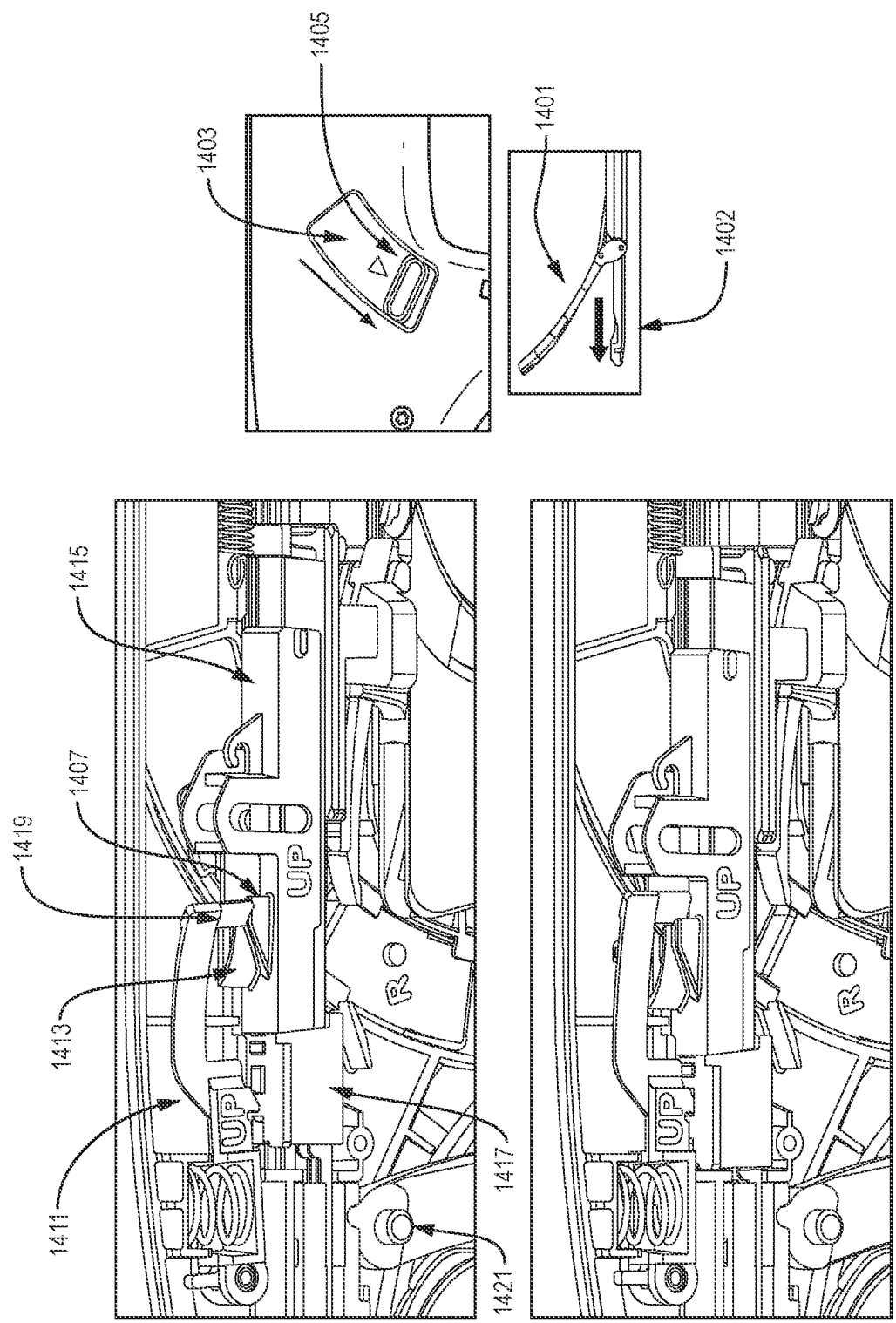
Figure 14C:
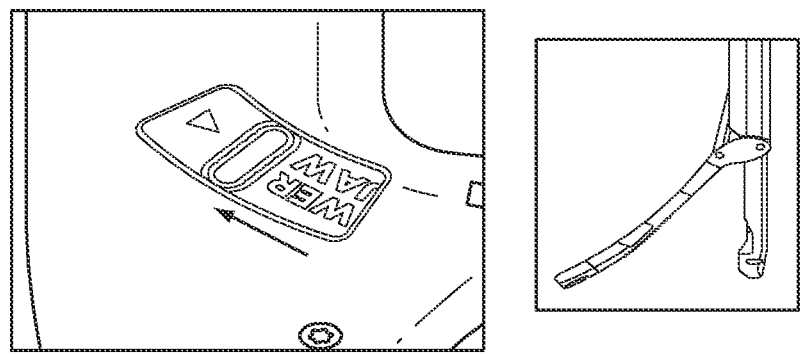
Figure 14C:
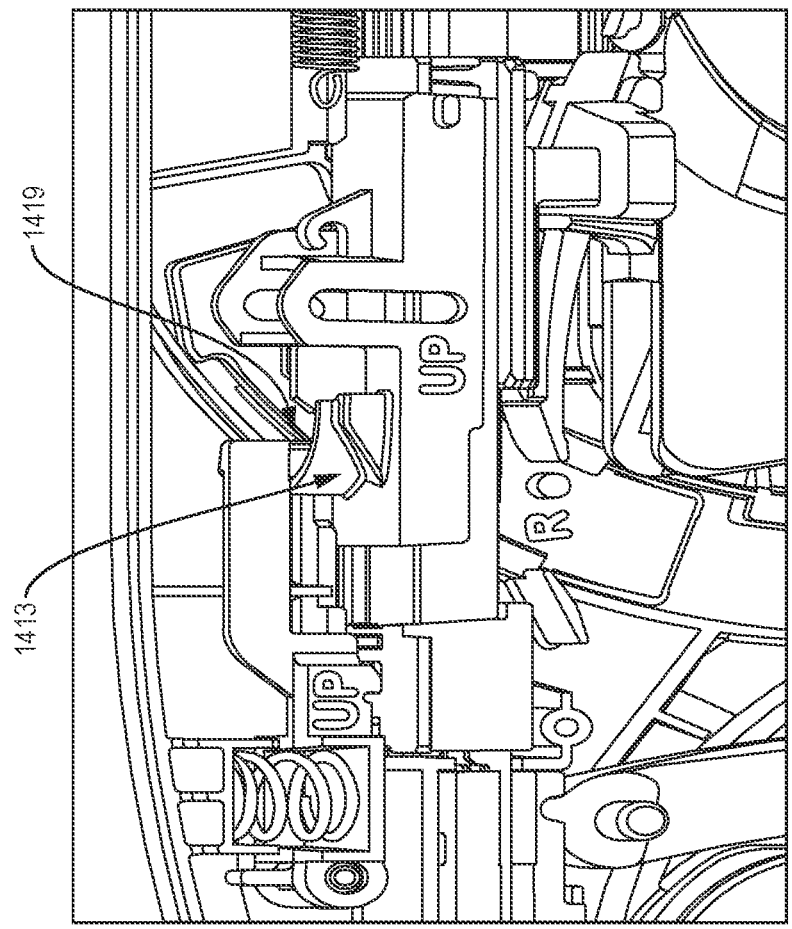

FIGS. 14A-14C illustrate the mechanical operation of functional internal components of a suture passer for extending a second jaw member 1402 when a thumb trigger 1403 is pushed forward. FIG. 14A corresponds to a position with second jaw 1402 fully retracted and the thumb trigger in a most retracted configuration (position 1), such that push button 1405 is retracted and only first jaw member 1401 extends from body. Detent first tooth (proximal tip) 1419 is distally and axially disposed relative to curved rib 1413 and ramp 1407 and second tooth 1421 is distally and axially spaced away from carriage member 1417. When thumb trigger 1403 is moved along its pathway, thumb trigger protrusion member engaged within slot of sleeve member 1415, moving the sleeve 1415 forward (distally) as shown in FIG. 14B, which simultaneously pushes the carriage member 1417 forward and thereby extends the lower jaw 1402. Detent member 1411 comprises a flexible arm as disclosed in previous figures that flexes laterally around a first ramp side of curved rib 1413 on the sleeve, and up ramp 1407. Engagement with ramp 1407 is maintained with biasing member at least partially disposed in nest 1004. Once the carriage member 1417 is fully advanced, the second detent tooth 1421 engages carriage opening to keep the second jaw member 1402 extended. First tooth 1419 is now on the other side of curved rib 1413 and ramp 1407 and may rest against rib 1109 (best seen in FIG. 11B). Release of the thumb trigger 1403 guides the first tooth 1419 between curved rib 1413 and rib 1109 best seen in FIG. 14C and thumb trigger rests in position 2 (as shown in FIG. 8A). With engagement of second tooth 1421 release of thumb trigger 1403 at this stage does not retract lower jaw 1402, as the carriage 1417 is inhibited from retracting by first and second teeth (1419 and 1421) and corresponding mating features in the carriage and sleeve.

Also shown in FIG. 14C, when the thumb trigger 1403 is released, a spring at a proximal end of sleeve pulls the sleeve member 1415 back against a proximal end of the carriage member 1417, holding the sleeve member 1415 and thumb triggers 1403 in an intermediate position. (Spring is not shown coupled to sleeve member in the figures throughout, but is looped around hook adjacent the slot of sleeve member so as to maintain a proximal bias on the sleeve member). There may me a lip, protrusion or blocking means at a proximal end of the carriage member 1417 to prevent the sleeve member 1415 from sliding off the carriage member 1417. A lip can be seen in FIG. 13 and a proximal end of carriage, configured to limit sliding of sleeve member. In this intermediate position, the first detent tip 1419 remains behind the curved rib 1413 and distally and axially disposed relative to ramp 1108 of the sleeve member 1415.

Figure 15A:
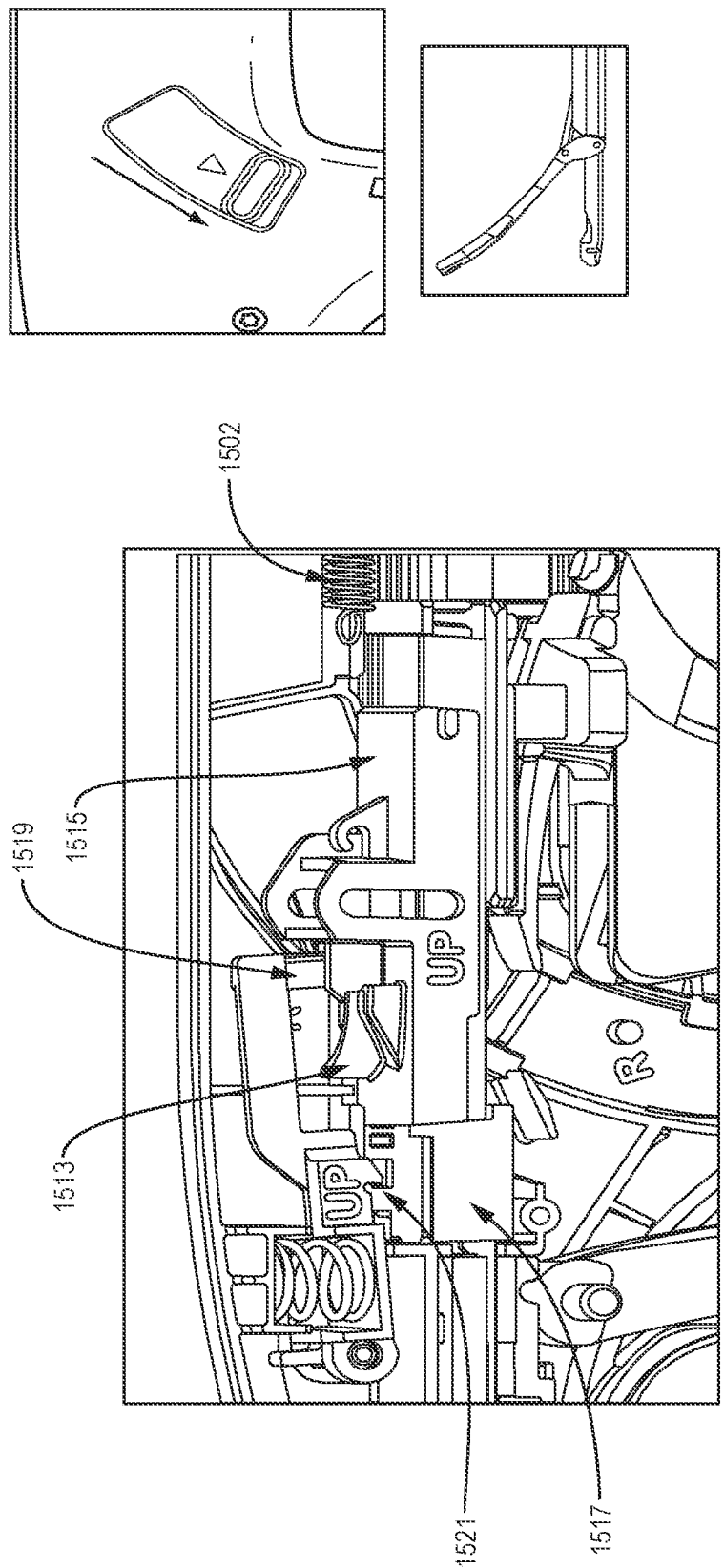
Figure 16A:
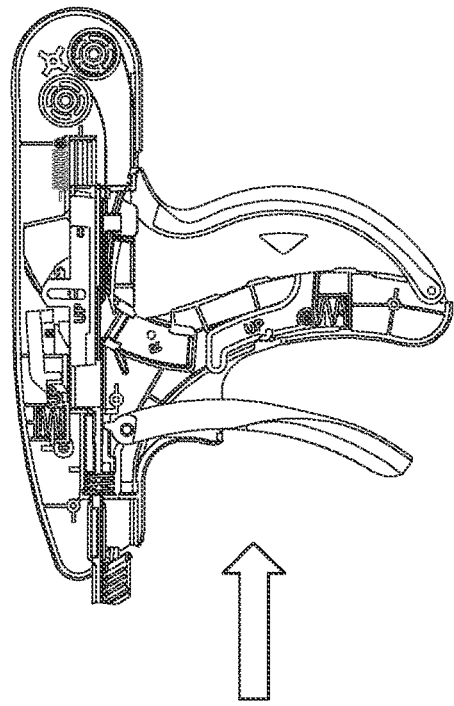
FIG. 16 illustrates section views (A, B, C and D) of a suture passer and operation to prevent a second jaw member retraction while the tissue penetrator is extended.
Figure 16B:
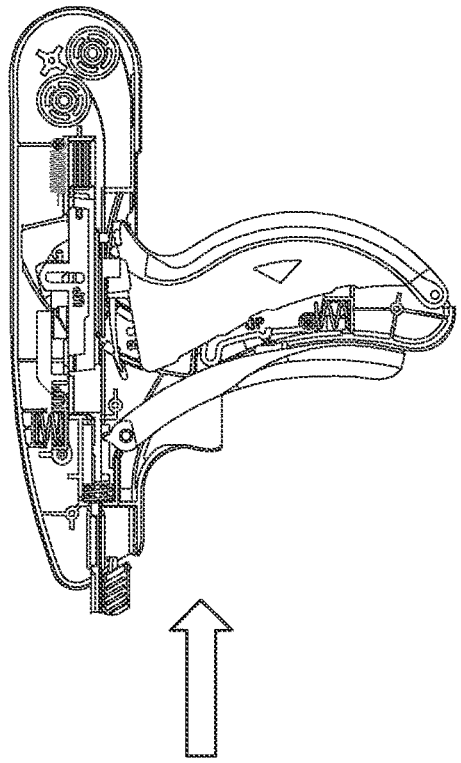
Figure 16C:
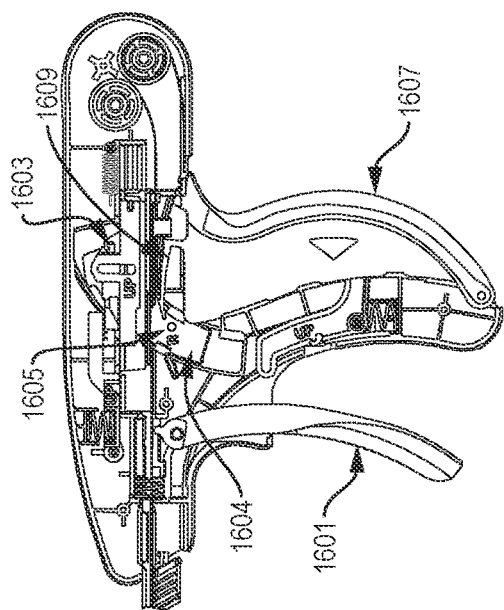
Figure 16D:
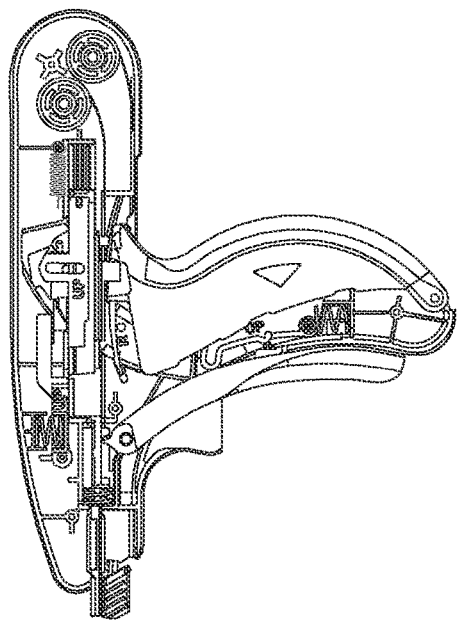

FIGS. 15A-15B illustrate the operation of second jaw retraction when a thumb trigger is pressed forward again to position 3. When thumb trigger is pressed forward again, tip 1519 of the detent member slides up a second ramp 1108 on the sleeve member 1515, the second ramp 1108 configured to elevate a portion of detent member 1511 so as to aid in removing and releasing the second detent tooth 1521 from opening in the carriage member 1517. The carriage member 1517 is then pulled backward by springs, retracting the second jaw member. As thumb trigger(s) are released and sleeve member 1515 returns, the detent tip 1519 flexes laterally around the end of the curved rib 1513 on the sleeve member 1515 and returns to its initial position in front of the rib.

In another aspect, the present disclosure provides a method for controlling a suture passer having a first jaw member extending from the distal end region of an elongated body and configured for angular movement relative to the elongated body, a second jaw member configured to form an opening with the first jaw member when the second jaw member is axially extended, and a thumb trigger actuated to retract or extend the second jaw member, the method includes: extending the second jaw by pushing the thumb trigger; and retracting the second jaw by pushing the thumb trigger.

In some embodiments of the method provided herein, the extending includes pushing the thumb trigger to actuate the sleeve member to move the carriage member forward to actuate the second jaw member to extend.

In some embodiments of the method provided herein, the retracting comprises pushing the thumb trigger to actuate the sleeve member to move the carriage member backward to actuate the second jaw member to retract.

In some embodiments of the method provided herein, the thumb trigger is connected to the outer surface of a sleeve member, wherein the inner surface is connected with a carriage member, wherein the carriage member actuates the second jaw member to extend or retract.

In some embodiments of the method provided herein, the carriage member is engaged with a detent member to extend a second jaw member.

In some embodiments of the method provided herein, the carriage member is disengaged from a detent member to retract a second jaw member.

In some embodiments of the method provided herein, the method further includes passing a tissue penetrator between the first and second jaw members when the first jaw member is at least partially clamped with the second jaw member, whereby the tissue penetrator is prevented from being passed from without clamping the jaws.

In some embodiments of the method provided herein, a suture is passed by the tissue penetrator deployable held with a distal tip retracted entirely within either the first or the second jaw member, whereby the suture is prevented from being passed from without clamping the jaws.

In another aspect, the present disclosure provides a suture passer device, wherein the device is designed to prevent retraction of the second jaw member when the tissue penetrator is being extended. The device includes an elongated body having a proximal end region and a distal end region; a first jaw member extending from the distal end region of the elongated body; a second jaw member configured to extend axially relative to the elongated body, wherein the second jaw is configured to form an opening with the first jaw member when the second jaw member is axially extended; a tissue penetrator trigger configured to extend a tissue penetrator between the first and second jaw members when actuated; and a thumb trigger configured to retract or extend the second jaw member when actuated, wherein when the tissue penetrator is extended, the second jaw member is blocked from retracting.

In some of the embodiments of the device provided herein, the thumb trigger includes a protrusion member extended above a first surface of the thumb trigger, when engaged with the actuated tissue penetrator trigger, the protrusion member restricting the actuation of the thumb trigger to retract the second jaw.

In some of the embodiments of the device provided herein, the tissue penetrator trigger comprises an interference member adjacent to the first surface of the thumb trigger, said interference member interacting with the protrusion member to block the actuation of the thumb trigger to retract a second jaw member.

In some of the embodiments of the device provided herein, the first jaw member is configured for angular movement relative to the elongated body.

In some embodiments, the device further includes a clamp trigger configured to actuate clamping of the first and second jaw members.

In another aspect, the disclosure provides a method for preventing damage to a tissue when using a suture passer device having a first jaw member extending from the distal end region of an elongated body, a second jaw member configured to extend axially relative to the elongated body, wherein the second jaw is configured to form an opening with the first jaw member when the second jaw member is axially extended, a tissue penetrator trigger configured to extend a tissue penetrator between the first and second jaw members when actuated, and a thumb trigger configured to retract or extend the second jaw member when actuated, the method including: blocking the thumb trigger from actuating to retract the second jaw member when a tissue penetrator is extended.

In some embodiments of the method provided herein, the blocking includes: pushing the thumb trigger to extend the second jaw; and pressing the tissue penetrator trigger to extend the tissue penetrator, whereby the thumb trigger is blocked from retracting the second jaw member.

In some embodiments of the method provided herein, the blocking includes restricting the actuation of the thumb trigger by engaging the tissue penetrator trigger with a protrusion member extended above a first surface of the thumb trigger, whereby the actuation of the thumb trigger to retract a second jaw member is blocked.

In some embodiments of the method provided herein, the tissue penetrator trigger includes an interference member adjacent to the first surface of the thumb trigger, the interference member interacting with the protrusion member to block the actuation of the thumb trigger to retract a second jaw member.

FIG. 16 illustrates the operation of a suture passer to prevent a second jaw member retraction while the tissue penetrator is extended. Suture passer includes clamp trigger 1601 and tissue penetrating trigger 1607. Retracting the second jaw member in the suture passer is performed by pressing a thumb trigger forward. The design includes protrusion members 1605 on each of the thumb triggers that sweep through the path of the tissue penetrator trigger 1607. When the tissue penetrator trigger 1607 is fully back and the tissue penetrator is therefore not extended, the protrusion members 1605 are not blocked and the thumb trigger can be actuated to retract the second jaw member. When the tissue penetrator trigger 1607 moves forward as shown in step C of FIG. 16 to extend the tissue penetrator, the tissue penetrator trigger blocks the protrusion members 1605. More specifically surface(s) such as interference surfaces 404 in FIG. 4 moves across a trajectory of the protrusion member 1605, inhibiting thumb trigger retraction. Of note, in order to retract lower jaw, the thumb trigger is first pushed to position 2 before release, and therefore protrusion 1605 must first move beyond surface 404 to retract the lower jaw. Surface 404 limits the actuation of the thumb trigger and therefore prevents retraction of the second jaw members. In Step D protrusion 1605 is shown abutting surface 404 so as to be inhibited from advancing (and thereby releasing first and second tooth of detent member).

In another aspect, the present disclosure provides a method for preventing damage to a tissue when using a suture passer device having a first jaw member extending from the distal end region of an elongated body, a second jaw member configured to extend axially relative to the elongated body, wherein the second jaw is configured to form an opening with the first jaw member when the second jaw member is axially extended, a tissue penetrator trigger configured to extend a tissue penetrator between the first and second jaw members when actuated, and a thumb trigger configured to retract or extend the second jaw member when actuated, the method including: blocking the thumb trigger from actuating to retract the second jaw member when a tissue penetrator is extended.

In some embodiments of the method provided herein, the blocking includes: pushing the thumb trigger to extend the second jaw; and pressing the tissue penetrator trigger to extend the tissue penetrator, whereby the thumb trigger is blocked from retracting the second jaw member.

In some embodiments of the method provided herein, the blocking includes restricting the actuation of the thumb trigger by engaging the tissue penetrator trigger with a protrusion member extended above a first surface of the thumb trigger, whereby the actuation of the thumb trigger to retract a second jaw member is blocked.

In some embodiments of the method provided herein, the tissue penetrator trigger includes an interference surface adjacent to the first surface of the thumb trigger, said interference surface interacting with the protrusion member to block the actuation of the thumb trigger to retract a second jaw member.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A suture passer device comprising:
an elongated body having a proximal end and distal end, the proximal end coupled to a handle;
a first jaw member coupled to the distal end of the elongated body and configured for angular movement relative to the elongated body;
a second jaw member configured to form an opening with the first jaw member;
a clamp trigger defining a portion of the handle, the clamp trigger configured to move the first jaw member between an open configuration and a clamped configuration, where the first and second jaw members are angularly closer to each other in the clamped configuration than the open configuration;
a tissue penetrator trigger defining a portion of the handle, the tissue penetrator trigger configured to selectively extend a tissue penetrator between the first and second jaw members; and
a lock disposed between the clamp trigger and the tissue penetrator trigger, including a first surface configured to interact with the clamp trigger and a second surface configured to engage the tissue penetrator trigger to prevent the tissue penetrator from extending when the first jaw member is in the open configuration until the first jaw member is in the clamped configuration.

2. The suture passer device of claim 1, wherein the second jaw member is configured to extend and retract axially relative to the elongated body.

3. The suture passer device of claim 1, wherein the first surface is configured to interact with the clamp trigger to disengage the second surface from the tissue penetrator trigger.

4. The suture passer device of claim 1, wherein the clamp trigger includes a surface configured to engage the first surface of the lock while moving the first jaw member towards the clamped configuration, so as to rotate the lock and disengage the second surface from the tissue penetrator trigger.

5. The suture passer device of claim 1, wherein the clamped configuration defines a predetermined angular opening between the first and second jaw member.

6. The suture passer device of claim 5, wherein the predetermined angular opening is between 5 degrees and 85 degrees.

7. The suture passer device of claim 6 wherein the first jaw member comprises a tissue penetrator receiving region for receiving and capturing the tissue penetrator, and wherein the predetermined angular opening defines a maximum opening such that the tissue penetrator extends from the second jaw member and through the tissue penetrator receiving region.

8. A suture passer device comprising:
an elongated body having a proximal end region and a distal end region;
a first jaw member coupled to the distal end region of the elongated body and configured for angular movement relative to the elongated body;
a second jaw member configured to extend axially relative to the elongated body, wherein the second jaw member is configured to form an opening with the first jaw member when the second jaw member is an extended configuration; and
a handle at the proximal end region including
a thumb trigger configured to be actuated in a first direction to both extend and retract the second jaw member; and
a sleeve member and a carriage member housed within the handle and operatively coupled to each other and also operatively coupled to the second jaw member, wherein the thumb trigger is communicably coupled to the sleeve, such that actuating the thumb trigger axially moves the sleeve member, carriage member and thereby second jaw member.

9. The suture passer device of claim 8, further comprising a detent member housed within the handle and configured to engage with an opening of the carriage member to hold the second jaw member in the extended configuration.

10. The suture passer device of claim 9, wherein the detent member is configured to disengage from the carriage member opening during retraction of the second jaw member.

11. The suture passer device of claim 9, wherein the detent member further comprises a tip configured to interact with a curved rib and ramp disposed on a top surface of the sleeve member such that actuation of the thumb trigger to extend the second jaw member slides the sleeve member so that the tip moves from a first side of the curved rib and ramp, to a second side of the curved rib and ramp and wherein releasing of the thumb trigger to an intermediate position maintains the extended configuration of the second jaw member with the tip remaining on the second side.

12. The suture passer device of claim 8 wherein the handle also includes a tissue penetrator trigger, the tissue penetrator trigger configured to move to an advanced configuration and move a tissue penetrator operatively coupled thereto across the opening between the first and second jaw members; and wherein in the advanced configuration a surface of the thumb trigger and a surface of the tissue penetrator trigger are engaged to prevent the second jaw member from retracting.

13. A suture passer device comprising:
an elongated body having a proximal end region and a distal end region;
a first jaw member extending from the distal end region of the elongated body;
a second jaw member configured to extend axially relative to the elongated body,
wherein the second jaw member is configured to form an opening with the first jaw member when the second jaw member is axially extended; and
a handle at the proximal end region, the handle including;
a tissue penetrator trigger configured to extend a tissue penetrator between the first and second jaw members when actuated; and
a thumb trigger configured to retract and extend the second jaw member when actuated, wherein when the tissue penetrator is extended, the second jaw member is blocked from retracting;
wherein the thumb trigger comprises a protrusion member extended above a first surface of the thumb trigger, said protrusion member configured to restrict actuation of the thumb trigger to retract the tissue penetrator;
wherein the tissue penetrator trigger comprises an interference surface adjacent to the first surface of the thumb trigger, said interference surface interacting with the protrusion member to block actuation of the thumb trigger to retract the second jaw member.

14. The suture passer device of claim 13, further comprising a clamp trigger configured to actuate clamping of the first and second jaw members.

15. The suture passer device of claim 14 further comprising a lock disposed between the clamp trigger and the tissue penetrator trigger, the lock including a first surface configured to interact with the clamp trigger and a second surface configured to interact with the tissue penetrator trigger, the lock configured to prevent the tissue penetrator from extending until the first and second jaw members defines an opening less than a predetermined opening.

\* \* \* \* \*